United States Patent
Nakazawa et al.

(10) Patent No.: US 7,198,758 B2
(45) Date of Patent: Apr. 3, 2007

(54) MICROARRAYING HEAD AND MICROARRAYER

(75) Inventors: Toji Nakazawa, Tokyo (JP); Akihiro Iimura, Tokyo (JP)

(73) Assignee: THK Co., Ltd., Tokyo (JP)

( * ) Notice: Subject to any disclaimer, the term of this patent is extended or adjusted under 35 U.S.C. 154(b) by 845 days.

(21) Appl. No.: 10/128,572

(22) Filed: Apr. 24, 2002

(65) Prior Publication Data

US 2002/0173048 A1    Nov. 21, 2002

(30) Foreign Application Priority Data

Apr. 26, 2001    (JP) .............................. 2001-129545
Apr. 26, 2001    (JP) .............................. 2001-129546

(51) Int. Cl.
*B01L 3/02*    (2006.01)
*G01N 1/10*    (2006.01)

(52) U.S. Cl. .................. 422/100; 422/63; 422/68.1; 436/180; 73/863.32; 73/864; 73/864.01; 73/864.11; 73/864.24; 73/864.25

(58) Field of Classification Search ............... 422/100, 422/63, 65–67, 68.1; 436/180; 73/863.32, 73/864, 864.01, 864.11, 864.25, 864.24
See application file for complete search history.

(56) References Cited

U.S. PATENT DOCUMENTS

| | | | |
|---|---|---|---|
| 4,258,761 A * | 3/1981 | Bennett, Jr. ................. | 141/242 |
| 5,756,050 A * | 5/1998 | Ershow et al. ............... | 422/100 |
| 6,001,311 A | 12/1999 | Brennan | |
| 6,024,925 A * | 2/2000 | Little et al. .................. | 422/100 |
| 6,101,946 A * | 8/2000 | Martinsky .................... | 101/494 |
| 6,170,494 B1 * | 1/2001 | Marinaro et al. ........ | 134/22.18 |
| 6,197,261 B1 * | 3/2001 | Linville et al. .............. | 422/104 |
| 6,506,611 B2 * | 1/2003 | Bienert et al. ............... | 436/180 |
| 6,605,257 B1 * | 8/2003 | Nakazawa et al. ........... | 422/100 |
| 6,629,626 B1 * | 10/2003 | Horsman et al. ............. | 222/420 |
| 6,767,748 B2 * | 7/2004 | Yokokawa et al. .......... | 436/180 |
| 6,833,113 B2 * | 12/2004 | Sentoh ......................... | 422/100 |
| 6,835,352 B2 * | 12/2004 | Ito et al. ...................... | 422/100 |
| 2004/0062686 A1 * | 4/2004 | Ganz et al. ................... | 422/100 |
| 2004/0072365 A1 * | 4/2004 | Rose et al. ................... | 436/180 |
| 2004/0089330 A1 * | 5/2004 | Muller .................... | 134/167 R |
| 2004/0096984 A1 * | 5/2004 | Elverd et al. ................ | 436/180 |

FOREIGN PATENT DOCUMENTS

EP        1075869 A1    2/2001

* cited by examiner

*Primary Examiner*—Brian R. Gordon
(74) *Attorney, Agent, or Firm*—Westerman, Hattori, Daniels & Adrian, LLP.

(57) ABSTRACT

A microarraying head 51 has a base portion 57 and a plurality of needles 53. The needles 53 are arranged in parallel with one another on the base portion 57. The needles 53 place a solution on substrates 3 with the top ends of the needles 53 touching substrates 3. Then, the needles 53 retain the solution including biological samples and form spots of the solution on the substrates 3. A space 58 for supplying cleansing fluid or the like is provided in the base portion 57 so as to extend all over the plurality of needles 53. Since the plurality of needles 53 can be all cleansed with substantially uniform pressure applied thereto, all the plurality of needles 53 can cleansed surely in a short time.

9 Claims, 17 Drawing Sheets

MICROARRAYING HEAD AND MICROARRAYER

BACKGROUND OF THE INVENTION

1. Field of the Invention

The present invention relates to a microarrayer for sequencing a large number of biological samples such as DNA fragments or oligonucleotides on substrates.

2. Description of the Related Art

Currently, technological development for analyzing the whole gene functions of a wide variety of organisms is in progress. DNA microarrays (that is, DNA chips) are of a large number of spots including DNA fragments or the like sequenced on glass slides or silicon substrates. Such DNA microarrays are very effective in analyzing gene expressions, genetic mutations, genetic variations, and the like.

Each substrate generally measures 1 cm$^2$ to several tens of cm$^2$, and several thousands to several hundred thousands of spots of DNA fragments are sequenced in this area. Each of the DNA fragments on the substrate is investigated with a fluorescent-labeled DNA complementary thereto. Fluorescence is generated when hybridization is produced between the DNA fragment on the substrate and the fluorescent-labeled DNA. The spot with which the fluorescence is generated is detected by a fluorescent scanner or the like, and a fluorescent image is analyzed. Thus, gene expressions, genetic mutations, genetic variations, and the like, can be analyzed.

To develop such DNA microarraying technology, a microarrayer for sequencing spots of DNA fragments densely on a substrate is required.

A microarrayer for sequencing DNA fragments adjusted in advance on a substrate is disclosed in Japanese Patent Laid-Open 503841/1998. In this apparatus, samples are retained in an open capillary flow channel formed between a pair of elongated members while a top end of a head constituted by the pair of elongated members is slightly stamped on a substrate so as to place a spot on the substrate. There is also known a head other than this head. That is, the head is constituted by a solution reservoir portion for retaining a solution, and a placing portion (for example, a pin or a needle) for placing spots on a substrate.

As for the performance of microarrayers, it is a requirement that spots of various DNA samples can be formed quantitatively in given places and with a size ranging from several tens of microns to several hundreds of microns. It is also a requirement that microarrays can be produced quickly in order to produce a large number of replicas.

In such a microarrayer, when a head terminates a work of forming spots of a solution and then retains a next solution different in kind from the previous solution, it is necessary to cleanse the head so as to prevent the previous solution from mixing into the next solution. In the head, there are often provided a plurality of placing portions (for example, pins or needles) for simultaneously forming spots on a plurality of substrates. To prevent the solutions from mixing with each other, all the plurality of placing portions have to be cleansed surely.

When a head which has finished a work of forming spots of a solution is made to retain a next solution of another kind in such a microarrayer, it is necessary to cleanse and dry the head so as to prevent the previous solution from mixing into the next solution. That is, a work of cleansing and drying the head becomes essential after the work of forming spots.

The work of forming spots is however suspended during the work of cleansing and drying the head. In addition, the time required for the work of cleansing and drying is generally longer than the time required for the work of forming the spots. It is therefore difficult to improve the working efficiency.

SUMMARY OF THE INVENTION

The present invention has been made under the above circumstances, and therefore an object of the invention is to provide a microarraying head and a microarrayer in which a plurality of placing portions for placing spots on substrates can be cleansed surely.

Another object of the present invention is to provide a microarrayer and a microarraying process in which the work of forming spots and the work of cleansing and drying a microarraying head can be carried out simultaneously so that microarrays can be produced extremely efficiently.

Description will be made below about the invention. Incidentally, the reference numerals in the accompanying drawings will be attached and placed between parentheses in order to make the invention easy to understand. The invention is, however, not limited to any illustrated mode.

In order to solve the foregoing problem, the present inventor has developed a microarraying head including a base portion and a plurality of placing portions arranged in parallel with one another on the base portion, wherein a broad space for supplying cleansing fluid or the like is provided in the base portion so as to extend all over the plurality of placing portions.

That is, according to the invention, the problem is solved by a microarraying head (51) for retaining a solution including biological samples, and forming spots of the solution on substrates. The microarraying head (51) has a base portion (57), and a plurality of placing portions (53) arranged in parallel with one another on the base portion (57) and for placing the solution on the substrates (3) with top ends of the placing portions (53) touching the substrates (3), while a space (58) for supplying cleansing fluid or the like is provided in the base portion (57) so as to extend all over the plurality of placing portions (53).

According to the invention, all the plurality of placing portions can be cleansed with substantially uniform pressure applied thereto. Thus, all the plurality of placing portions can be cleansed surely in a short time.

In addition, according to the invention, the microarraying head (51) further includes a plurality of solution reservoir portions (52) for retaining the solution including the biological samples. In the microarraying head (51), the placing portions (53) haunt the solution reservoir portions (52) so as to place the solution retained in the solution reservoir portions (52) onto the substrates (3); the solution reservoir portions (52) are attached to the base portion (57); and the space (58) for supplying cleansing fluid or the like communicates with the solution reservoir portions (52).

According to the invention, all the interiors of the plurality of solution reservoir portions can be cleansed with substantially uniform pressure applied thereto.

Further, according to the invention, in the microarraying head (51), the placing portions (53) are arranged lengthwise and crosswise on the base portion (57).

For example, when a narrow pipe-like channel is prepared as a channel for supplying the cleansing fluid to the placing portions, the channel resistance of the pipe-like channel increases. Thus, the cleansing fluid is sprayed with great force onto placing portions on one end side, while the spraying force becomes weaker as the cleansing fluid goes to the other end side. In the worst case, there is a possibility that placing portions on the other end are not cleansed sufficiently. In the case where cleansing is not carried out sufficiently, there occurs a disadvantage that solutions are mixed with each other when a next solution is retained in the placing portions. According to the invention, since the space for supplying cleansing fluid or the like extends all over the placing portions arranged lengthwise and crosswise, all the plurality of placing portions can be cleansed with substantially uniform pressure applied thereto.

Further, according to the invention, a microarrayer may be also formed as follows. That is, the microarrayer includes a solution reservoir portion (74) for retaining a solution including biological samples; a working table (4) on which a plurality of substrates (3) can be arrayed; a solution retaining unit (51) for retaining the solution taken in from the solution reservoir portion (74), and forming spots of the solution on the substrates (3); a cleansing and other treatment portion (71, 72, 73) for carrying out cleansing and other treatment on the retaining unit (51); a moving unit (23, 95) for moving the retaining unit (51) close to/far from the substrates (3) and making the retaining unit (51) form spots on the substrates (3); and a conveying unit (6, 75) for conveying the retaining unit (51) in an area including the solution reservoir portion (74), the working table (4) and the cleansing and other treatment portion (71, 72, 73), and providing two-dimensional coordinates for the retaining unit (51); wherein the retaining unit (51) has a base portion (57), and a plurality of placing portions (53) arranged in parallel with one another on the base portion (57) and for placing the solution on the substrates (3) with top ends of the placing portions (53) touching the substrates (3); and wherein a space (58) for supplying cleansing fluid or the like is provided in the base portion (57) so as to extend all over the plurality of placing portions (53).

Also, in order to solve the foregoing problem, the present inventor prepared a microarraying head for an area for forming spots and a microarraying head for an area for cleansing and drying. Cleansing and other treatment were carried out on one microarraying head while spots were formed on substrates by the other microarraying head. Then, a configuration was made so that the microarraying heads could be delivered between the area for forming spots and the area for cleansing and drying.

That is, according to the invention, the foregoing problem is solved by a microarrayer including a solution reservoir portion (74) for retaining a solution including biological samples; a working table (4) on which a plurality of substrates (3) can be arrayed; a plurality of retaining units (51) for retaining the solution taken in from the solution reservoir portion (74), and forming spots of the solution on the substrates (3); a cleansing and other treatment portion (71, 72, 73) for carrying out cleansing and other treatment on one of the retaining units (51); a conveying unit (6, 75) for conveying one of the retaining units (51) in an area including the solution reservoir portion (74), the working table (4) and the cleansing and other treatment portion (71, 72, 73), and providing two-dimensional coordinates for the retaining unit (51). In the microarrayer, the plurality of retaining units (51) are provided; the conveying unit (6, 75) has a first conveying unit (75) for conveying one of the retaining units (51) onto the cleansing and other treatment portion, and a second conveying unit (6) for conveying one of the retaining units (51) onto the working table; and the retaining units (51) are delivered between the first conveying unit (75) and the second conveying unit (6).

According to the invention, cleansing and other treatment can be carried out on one retaining unit conveyed by the first conveying unit while spots are being formed on substrates by the other retaining unit conveyed by the second conveying unit. The work of forming spots on substrates can be kept in succession except the moment when the retaining units are delivered between the first conveying unit and the second conveying unit. Thus, microarrays can be produced extremely efficiently.

Incidentally, as the retaining unit, a system may be constituted by solution retaining portions for retaining a solution, and placing portions (for example, pins or needles) protruding from the solution retaining portions and for placing spots on substrates, as described in the following embodiment. However, other systems may be adopted. Examples of such other systems may include a pen system in which samples are retained in an open capillary channel formed between a pair of elongated members provided at a distance from each other like a pen nib, and the front ends of the pair of elongated members are made to abut against substrates mechanically; an ink jet system using the principle of an ink jet printer; and a capillary system using a capillary tube.

In addition, according to the invention, the microarrayer further includes a moving unit (23, 95) for moving one of the retaining units (51) close to/far from the substrates (3) and making the retaining unit (51) form spots on the substrates (3); wherein each of the retaining units (51) can be attached to the moving unit (23, 95) removably.

When the retaining unit retaining a solution is made to touch the substrates mechanically so as to form spots of the solution on the substrates, it is necessary to provide the moving unit for moving the retaining unit close to/far from the substrates.

In addition, according to the invention, in the microarrayer, the first conveying unit (75) or the second conveying unit (6) has a plurality of grasping portions (102) for grasping the retaining units (51), and a slewing portion (100) for slewing the plurality of grasping portions (102) so that one of the retaining units (51) can be delivered from the first conveying unit (75) to the second conveying unit (6) while one of the retaining units (51) can be delivered from the second conveying unit (6) to the first conveying unit (75).

According to the invention, the retaining units can be delivered between the first conveying unit and the second conveying unit directly without being once left on the microarrayer. Thus, the work of delivery can be performed efficiently.

Further, according to the invention, the microarrayer further includes a detection unit (67) for detecting a posture and/or a position of the retaining unit (51) supported by the second conveying unit (6); a posture and/or position changing unit (43, 6) for changing the posture and/or the position of the retaining unit (51) with respect to the second conveying unit (6); and a control unit for operating the posture and/or position changing unit (43, 6) based on the posture of the retaining unit (51) detected by the detection unit (67).

Whenever the retaining unit on the second conveying unit is replaced, the position of the retaining unit supported by the second conveying unit changes slightly. To form spots of the solution on the substrates correctly, the posture and/or the position of the retaining unit has to be corrected whenever the retaining unit is replaced. According to the invention, the replacing retaining unit can be corrected to have the same posture and/or the same position as those of the replaced retaining unit.

Further, according to the invention, in the microarrayer, the solution reservoir portion (74) has a plurality of solution retaining plates (121) for retaining the solution, a cassette (122) for receiving the solution retaining plates (121), and a plate conveying mechanism (123) for extracting one of the solution retaining plates (121) from the cassette (122) and conveying the extracted solution retaining plate (121) to a predetermined position.

According to the invention, the plate conveying mechanism extracts a required solution retaining plate from the arrangement of a large number of solution retaining plates, and conveys the extracted solution retaining plate to a predetermined position. In this predetermined position, a so-called load for immersing the retaining unit into a solution of biological samples so as to suck the solution is carried out. It is therefore possible to carrying out the load of required biological samples selected from a plurality of kinds of biological samples automatically.

Further, according to the invention, a microarraying process for sequencing spots of a solution of biological samples on substrates (3) can be also arranged as a microarraying process by including a stamping step of taking in and retaining a solution, using a second conveying unit (6) to convey a microarraying head (51) for forming spots of the solution on the substrates (3), and sequencing spots of the solution of biological samples on the substrates (3); a cleansing step of using a first conveying unit (75) to convey the microarraying head (51), and carrying out cleansing and other treatment on the microarraying head (51); and a delivering step for delivering microarraying heads (51) between the first conveying unit (75) and the second conveying unit (6), one of the microarraying heads (51) being supported by the first conveying unit (75), the other being supported by the second conveying unit (6); wherein the stamping step and the cleansing step are carried out simultaneously.

DETAILED DESCRIPTION OF THE PREFERRED EMBODIMENTS

Now, a description will be given in more detail of preferred embodiments of the invention with reference to the accompanying drawings.

Figure 1:
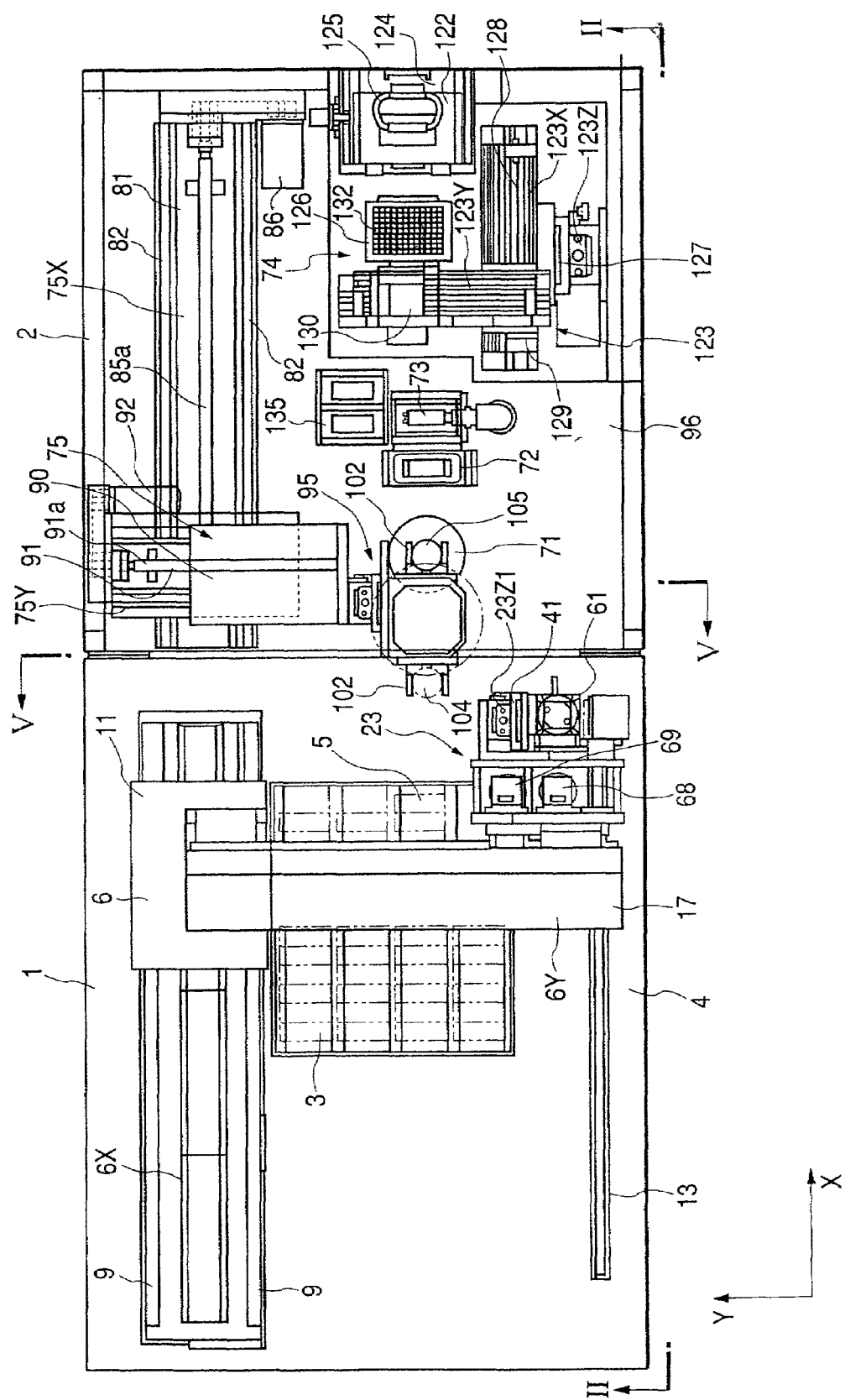
FIG. 1 is a plan view showing a microarrayer according to a first embodiment of the invention.
Figure 2:
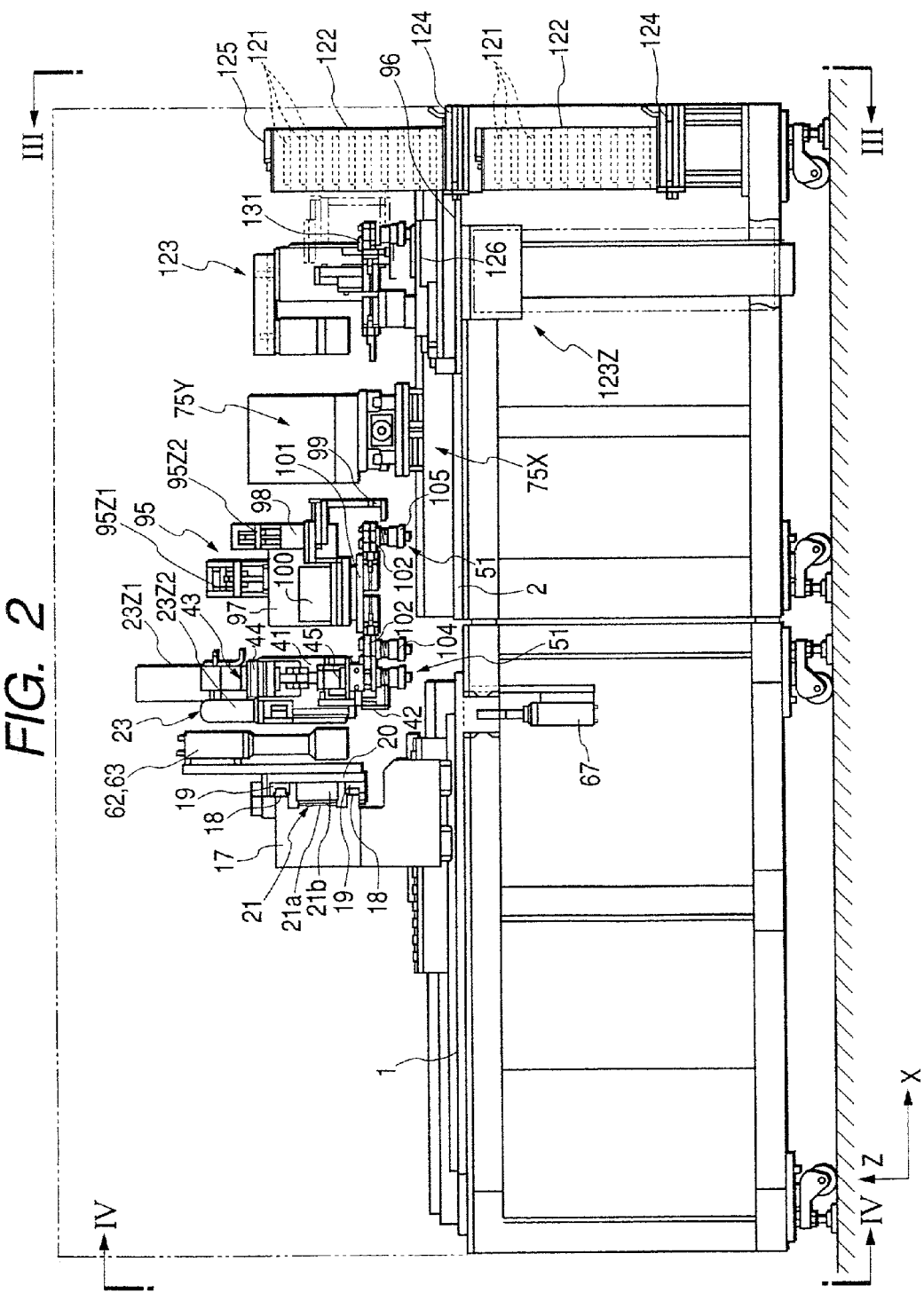
FIG. 2 is a front view of the microarrayer, taken on line II—II in FIG. 1.
Figure 3:
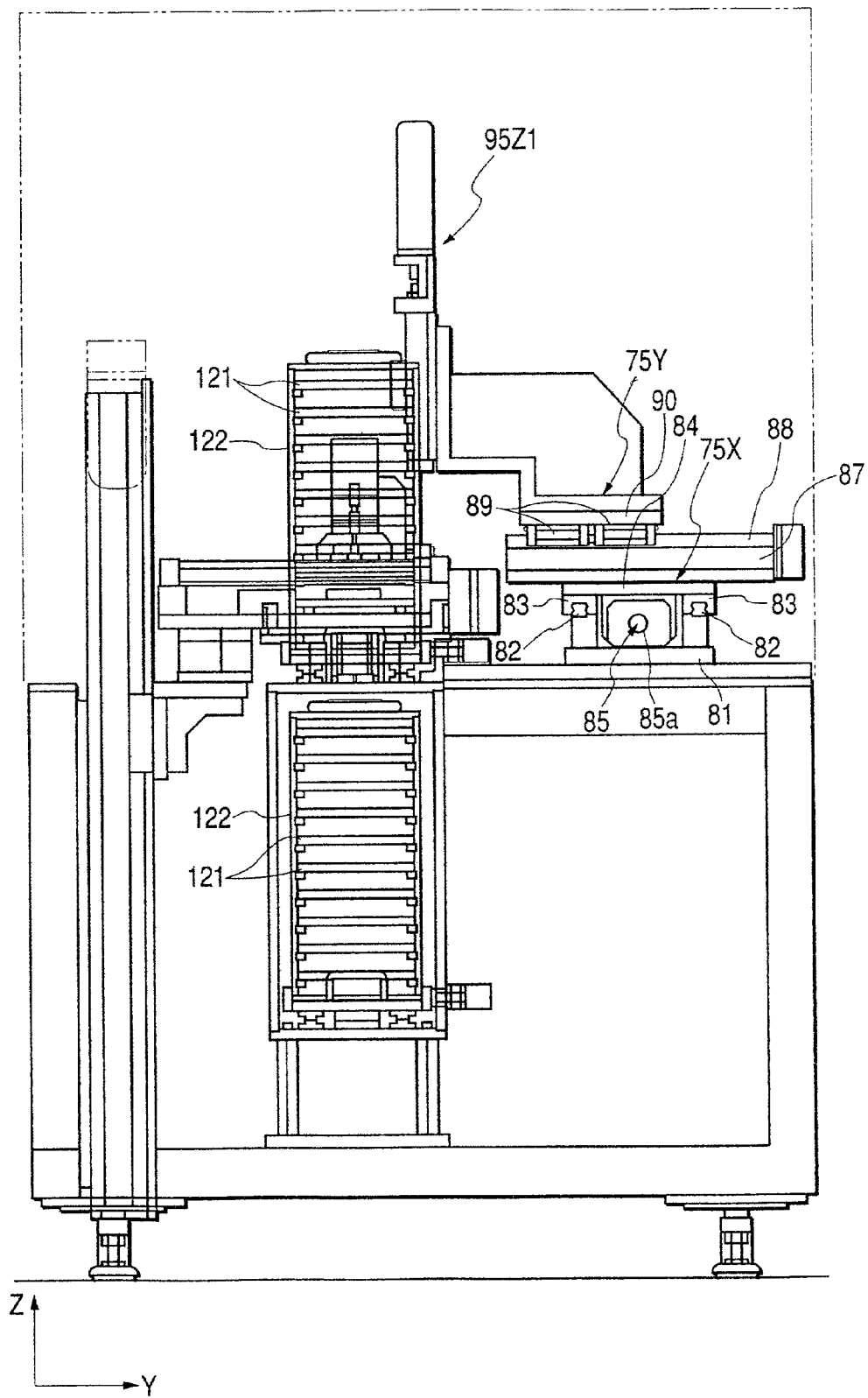
FIG. 3 is a right side view of the microarrayer, taken on line III—III in FIG. 2.
Figure 4:
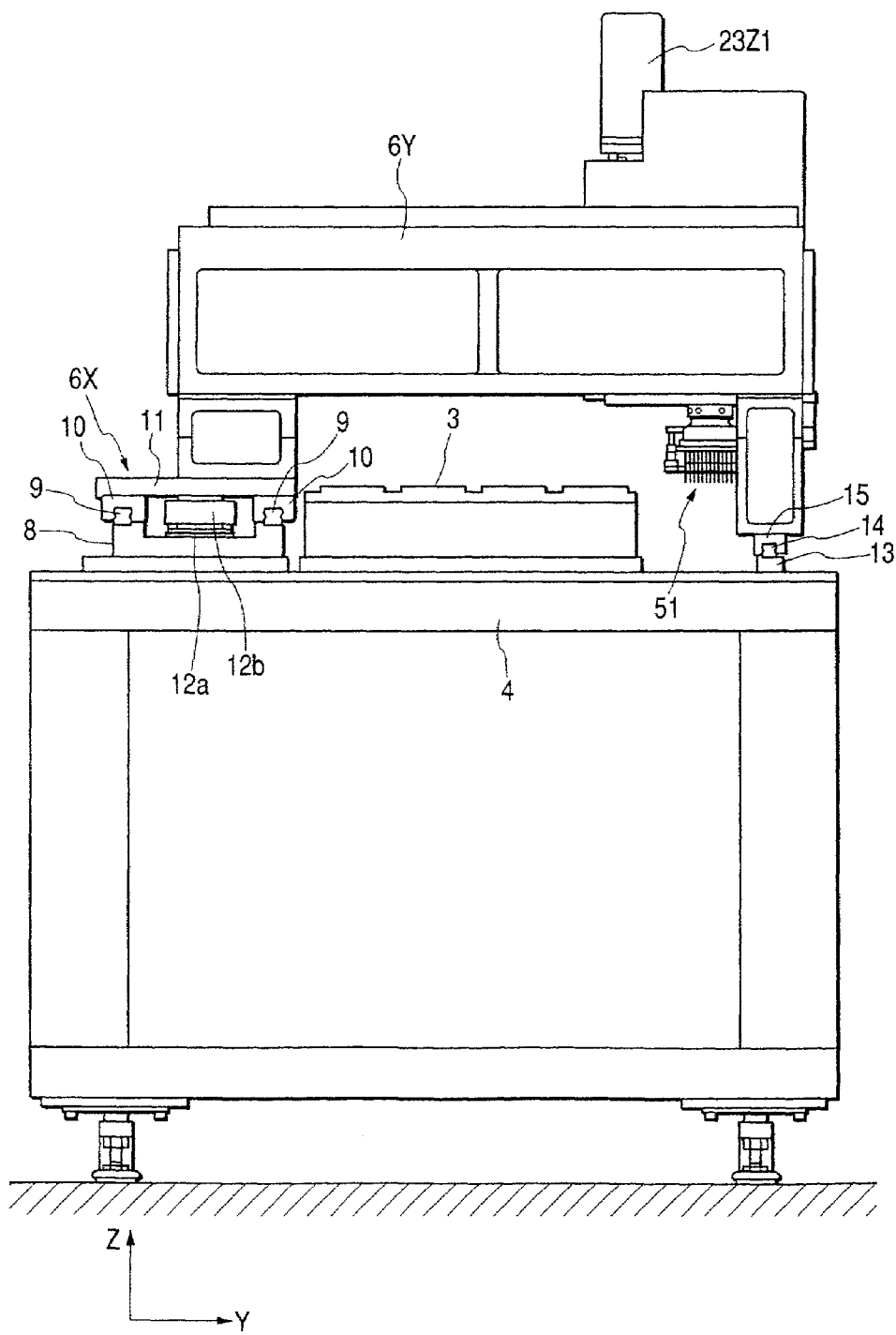
FIG. 4 is a left side view of the microarrayer, taken on line IV—IV in FIG. 2.
Figure 5:
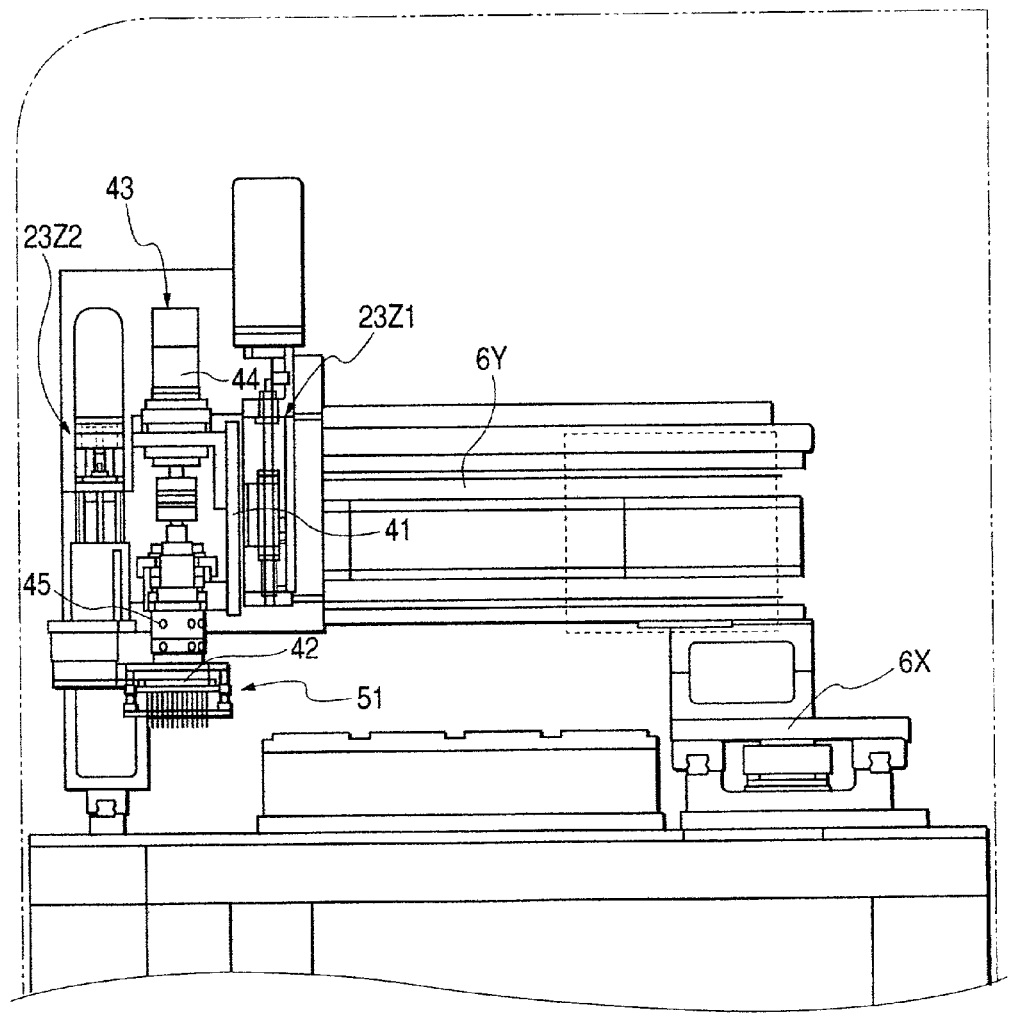
FIG. 5 is a sectional view of the microarrayer, taken on line V—V in FIG. 1.

FIG. 1 is a plan view of the microarrayer according to this embodiment. FIG. 2 is a front view of this apparatus taken on line II—II in FIG. 1. FIG. 3 is a right side view of this apparatus, taken on line III—III in FIG. 2. FIG. 4 is a left side view of the apparatus, taken on line IV—IV in FIG. 2. FIG. 5 is a sectional view of the apparatus, taken on line V—V in FIG. 1.

By this apparatus, a large number of spots of a solution of biological samples such as DNA fragments or oligonucleotides adjusted in advance are sequenced on a substrate made of slide glass, silicon or the like. Each substrate generally measures 1 cm$^2$ to several tens of cm$^2$, and several thousands to several hundred thousands of spots of DNA fragments are sequenced in this area. For example, each of the spots has a diameter ranging from several tens of microns to several hundreds of microns.

As shown in FIG. 1, the microarrayer has two areas. One is a stamping area 1 where a microarraying head 51 (hereinafter referred to as "head" simply) retaining a solution is stamped on substrates so that spots of the solution of biological samples are sequenced on the substrates. The other is a cleansing area 2 where the head 51 which has finished forming the spots is cleansed, and the cleansed head 51 is allowed to retain a next solution different in kind from the previous solution. The configuration of the head will be described later.

First, description will be made on the stamping area. A large number of substrates 3 are mounted on a working table 4 so as to form a matrix. In this embodiment, the substrates 3 are mounted in 48 sections in total arranged lengthwise in four lines and crosswise in 12 lines. The number of the substrates 3 can be changed variously in accordance with the number of replicas to be produced. The substrates 3 are made of slide glass, silicon, or the like, and the surfaces of the substrates 3 have been subjected to surface treatment so that biological samples can adhere to the surface of the substrates 3.

Suction holes are opened in the working table 4 correspondingly to the substrates respectively, while conduits of a not-shown vacuum system are connected to the suction holes. When the vacuum system is actuated, the air is sucked from the suction holes so that the substrates 3 . . . are fixed to the working table.

In a block of the working table 4, a test table 5 is provided so that two substrates or dummy substrates are mounted on the test table 5 for producing microarrays on trial. When needles of the head 51 retaining a solution are stamped on the substrates 3 suddenly, the needles to which the solution adheres excessively are stamped. To avoid this situation, the needles are stamped on the substrates 3 on the test table 5 so that the solution adhering to the needles excessively is flicked off the needles.

An XY-biaxially conveying mechanism 6 as a second conveying unit for conveying the head 51 and providing two-dimensional coordinates for the head 51 is attached onto the working table 4. This XY-biaxially conveying mechanism 6 positions the head 51 so that very small spots can be formed in given positions on the substrates 3, for example, so that the head 51 can be stamped on a position shifted by several hundreds of microns in the X-direction or the Y-direction from the position where the head 51 was stamped for the last time. In addition, the XY-biaxial conveying mechanism 6 moves to a delivery position 104 which will be described later, so as to receive the head 51, and conveys the head 51 to the delivery position 104 again after the head 51 has finished forming spots.

As shown in FIGS. 1 and 4, the XY-biaxially conveying mechanism 6 is constituted by an X-axially conveying mechanism 6X and a Y-axially conveying mechanism 6Y. The X-axially conveying mechanism 6X has a longitudinal fixed frame 8, a linear guide, a table 11 and a linear motor 12. The fixed frame 8 is provided to extend in the X-axis direction. The linear guide is constituted by rails 9 and 9 mounted on the fixed frame 8 so as to extend in the X-axis direction, and sliders 10 and 10 incorporated movably with respect to the rails 9 and 9. The table 11 is guided by the linear guide. The linear motor 12 drives the table 11. The linear motor 12 is constituted by a magnet 12a as a secondary side extending in the X-axis direction, and a coil 12b as a primary side attached to the back side of the table 11 so as to be opposed to the magnet 12a. A longitudinal fixed frame 13 and a linear guide are provided. The fixed frame 13 is provided to extend in the X-axis direction on the opposite side to the X-axially conveying mechanism 6X so as to interpose the substrates between the conveying mechanism 6X and the fixed frame 13. The linear guide is constituted by a rail 14 mounted on the fixed frame 13 so as to extend in the X-axis direction, and a slider 15 incorporated movably with respect to the rail 14.

As shown in FIGS. 1 and 2, the Y-axially conveying mechanism 6Y has a longitudinal movable frame 17, a linear guide, table 20 and a linear motor 21. The movable frame 17 is built between the slider 15 and the table 11 which is driven by the X-axially conveying mechanism 6X. The linear guide is constituted by rails 18 and 18 mounted on the movable frame 17 so as to extend in the Y-axis direction, and sliders 19 and 19 incorporated movably with respect to the rails 18 and 18. The table 20 is guided by the linear guide. The linear motor 21 drives the table 20. The linear motor 21 is constituted by a magnet 21a as a secondary side extending in the Y-axis direction, and a coil 21b as a primary side attached to the back side of the table 20 so as to be opposed to the magnet 21a.

A Z-axially driving mechanism 23 as a moving unit is supported on the XY-biaxially conveying mechanism 6. This Z-axially driving mechanism 23 moves the head 51 in the Z-axis direction orthogonal to the X-axis and the Y-axis, that is, in the direction in which the head 51 is made close to/far from the substrates 3. The Z-axially driving mechanism 23 has a Z1-axially driving mechanism 23Z1 for lifting the whole of the head 51 up/down, and a Z2-axially driving mechanism 23Z2 for protruding needles from solution reservoir members of the head 51.

Figure 6:
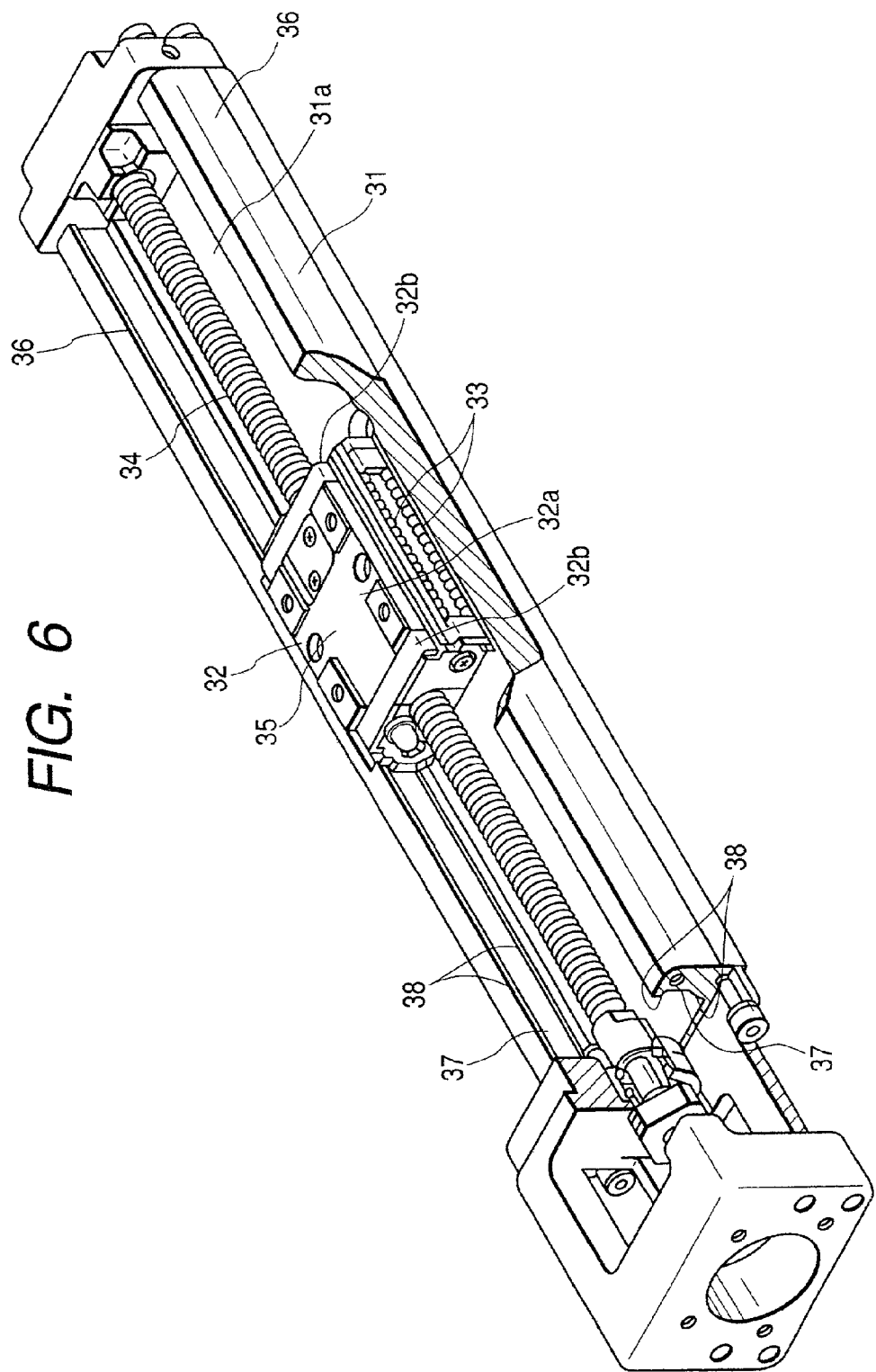
FIG. 6 is a perspective view showing an electric actuator.

The Z1-axially driving mechanism 23Z1 is constituted by an electric actuator for moving a slider by use of a feeding screw and an electric motor. As shown in FIG. 6, this electric actuator has a high-rigidity outer rail 31 having a U-shape in section, and a slider 32 incorporated in the outer rail 31 so that the slider 32 can reciprocate freely. A nut is integrally provided at the center of the slider 32, and a plurality of balls 33 . . . are provided for circulating between the opposite flanks of the slider 32 and the inner flanks of the outer rail 31. Since this electric actuator has an equal rated load in any direction in which the electric actuator acts on the slider 32, the electric actuator can be used suitably as a Z-axially driving mechanism for attaching the head 51 or the like to the slider in the state where the head 51 or the like is overhanging.

Detailed description will be made on the electric actuator constituting the Z1-axially driving mechanism 23Z1. The electric actuator has an outer rail 31, a slider 32 guided movably linearly by this outer rail 31, a nut 35 provided in this slider 32 so as to be screwed to a threaded shaft, and a threaded shaft 34 supported rotatably on the longitudinal opposite ends of the outer rail 31. A not-shown electric motor is attached to one end of the outer rail 31. The output shaft of the electric motor is coupled with the threaded shaft 34 through a joint.

The outer rail 31 has a U-shape in section, jetties 36 and 36 are provided on the top of the outer rail 31 so as to extend in parallel with and opposite to each other while a recess portion 31a is sandwiched between the jetties 36 and 36. Grooves 37 and 37 are provided in the inside flanks of the jetties 36 and 36 so as to extend over the whole lengths of the jetties 36 and 36. Two ball races 38 and 38 are formed in upper and lower corner portions of each groove 37.

The slider 32 is constituted by a block body 32a, and end plates 32b attached to the opposite end surfaces of the block body 32a. The slider 32 is inserted into the recess portion 31a on the top of the outer rail 31 and supported to be held between the jetties 36 and 36 through balls 33 . . . as rolling elements.

Load races, opposed to the ball races 38, of the outer rail 31 are provided in the opposite flanks of the block body 32a. The balls 33 . . . are interposed rollingly between the ball races 38 and the load races opposed respectively. In addition, in the block body 32a, clearance holes for returning balls rolling in the load zone are formed in parallel with the load races. Further, in each of the end plates 32b provided on the opposite sides of the block body 32a, a return passageway is provided for picking up the balls 33 . . . in the load zone and circulating the balls 33 . . . to the load zone again.

The nut to be screwed to the threaded shaft 34 is provided at the center of the block body 32a. A spiral load race corresponding to a spiral ball race formed in the threaded shaft 34 is formed in the nut. A plurality of balls as rolling elements are interposed rollingly between the spiral ball race and the spiral load race. A return tube for circulating the balls rolling in the load zone is provided in the nut.

As shown in FIGS. 1, 2 and 5, a table 41 is attached to the slider of the Z1-axially driving mechanism 23Z1. The Z2-axially driving mechanism 23Z2 is attached to the table 41. The Z2-axially driving mechanism 23Z2 is constituted by an electric actuator configured similarly to that of the Z1-axially driving mechanism 23Z1, but made smaller in scale than the Z1-axially driving mechanism 23Z1. An L-shaped arm 42 for moving the needles of the head 51 up/down is attached to the slider of the Z2-axially driving mechanism 23Z2. The L-shaped arm 42 is formed so that the L-shaped arm 42 can be plugged into the head 51 by a not-shown air cylinder (see FIG. 7). When the front end of the L-shaped arm 42 is plugged into the head 51 and the plugged L-shaped arm 42 is moved down by the Z2-axially driving mechanism 23Z2, the needles protrude from the solution reservoir members of the head 51.

A Θ-axially rotating mechanism 43 as a posture changing unit for changing the posture of the head 51 is attached to the table 41 of the Z1-axially driving mechanism 23Z1. This Θ-axially rotating mechanism 43 slews the head 51 in a horizontal plane. The Θ-axially rotating mechanism 43 has an electric motor 44 attached to the table 41, and a substantially cylindrical chuck portion 45 supported on the table 41 rotatably around the Z axis. The chuck portion 45 is coupled with the electric motor 44 through a joint. The chuck portion 45 grasps the head 51 removably.

Figure 7A:
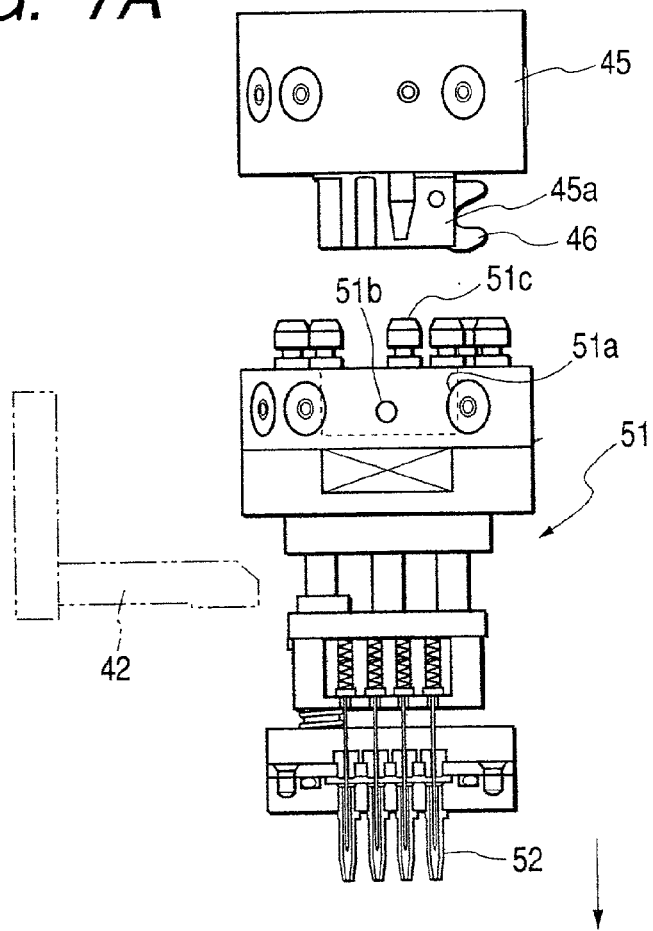
FIGS. 7A and 7B are views showing a chuck portion and a head, in which FIG. 7A showing the state where needles are lifted up, FIG. 7B showing the state where the needles are lifted down.
Figure 7B:
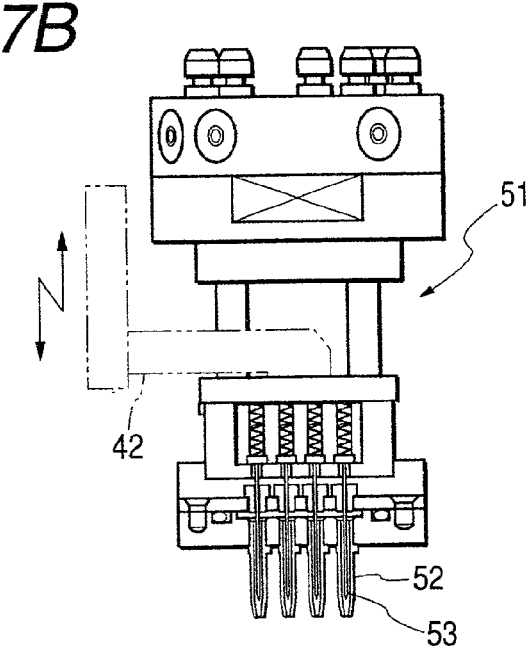

FIGS. 7A and 7B show the chuck portion 45 and the head 51. As shown in FIG. 7A, a fitting protrusion portion 45a fitting to the head 51 is formed in the lower portion of the chuck portion 45. Claws 46 . . . are provided circumferentially and rotatably at an equal interval on the protrusion portion 45a. The claws 46 . . . are rotated by a not-shown air cylinder. The fitting protrusion portion 45a of the chuck portion 45 is inserted into a fitting recess portion 51a of the head 51. When the claws 46 . . . are opened simultaneously to protrude laterally, the claws 46 . . . are engaged with a pin 51b provided on the fitting recess portion 51a of the head 51. Thus, the chuck portion 45 grasps the head 51. On the contrary, when the claws 46 . . . are closed inward, the engagement between the claws 46 and the pin 51b is released, and the head 51 is removed from the chuck portion 45. In addition, a plurality of positioning tapered pins 51c . . . are provided in the upper surface of the head 51 so that the head 51 can be positioned with respect to the chuck 45.

FIG. 7B shows the state where the front end of the L-shaped arm 42 has been plugged into the head 51. When the plugged L-shaped arm 42 is moved down by the Z2-axially driving mechanism 23Z2, needles 53 protrude from solution reservoir members 52 of the head 51.

As shown in FIG. 2, an image pickup element 67 (for example, CCD camera) as a detection unit for detecting the posture and position of the head 51 from below is provided in the working table 4. A replaced head 51 is first conveyed to above the image pickup element 67. A mark for indicating the position of the head 51 is pasted on the head 51. The image pickup element 67 detects this mark. Information about the posture and position of the head 51 detected by the image pickup element 67 is put into a controller as a control unit. The controller operates the Θ-axially rotating mechanism 43 as a posture changing unit and the XY-biaxially conveying mechanism 6 on the basis of the information about the posture and position of the head 5 so that the posture and position of the head 51 are kept constant even if the head 51 is replaced.

When the controller operates the Θ-axially rotating mechanism 43 so as to rotate the head 51 around the Z axis, the posture of the head 51 changes. On the other hand, when the controller operates the XY-biaxially conveying mechanism 6 so as to rotate the head 51 around the Z axis, the position of the head 51 changes. In such a manner, a head 51 used in place of a previous head 51 is corrected to take the same posture and position as those of the previous head 51. Thus, spots of the solution can be formed correctly on the substrates 3. Incidentally, an encoder functioning as an angle detection unit for detecting the rotation angle of the electric motor 44 is provided in the Θ-axially rotating mechanism 43. The rotation angle of the electric motor 44 is fed back so that the Θ-axially rotating mechanism 43 is controlled to rotate at a given angle.

In addition, a substrate image pickup element 68 (for example, CCD camera) and a spot image pickup element 69 (for example, CCD camera) are provided in the XY-biaxially conveying mechanism 6 so that spots can be formed in given positions on the substrates 3. The substrate image pickup element 68 detects the positions of the substrates 3 attached to the working table 4, and the spot image pickup element 69 detects the state of the spots formed on the substrates.

Figure 8:
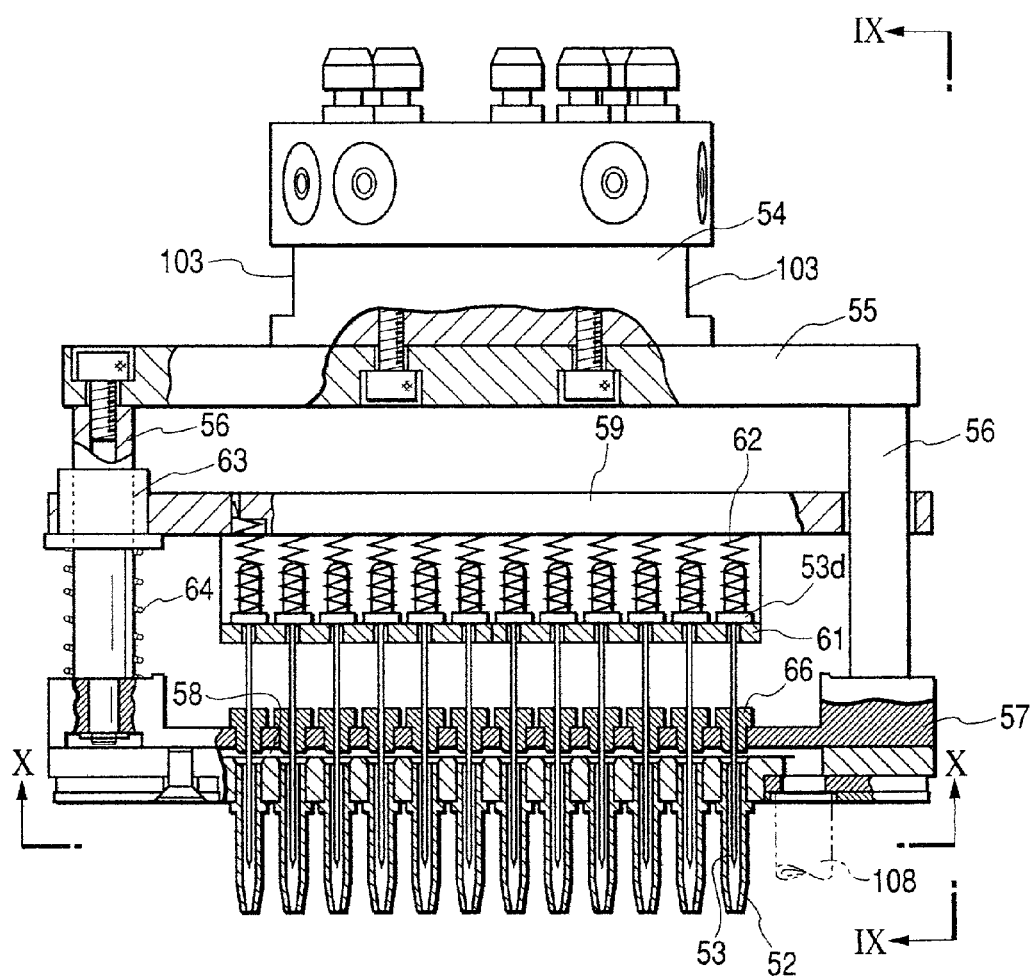
FIG. 8 is a front view of the head.
Figure 9:
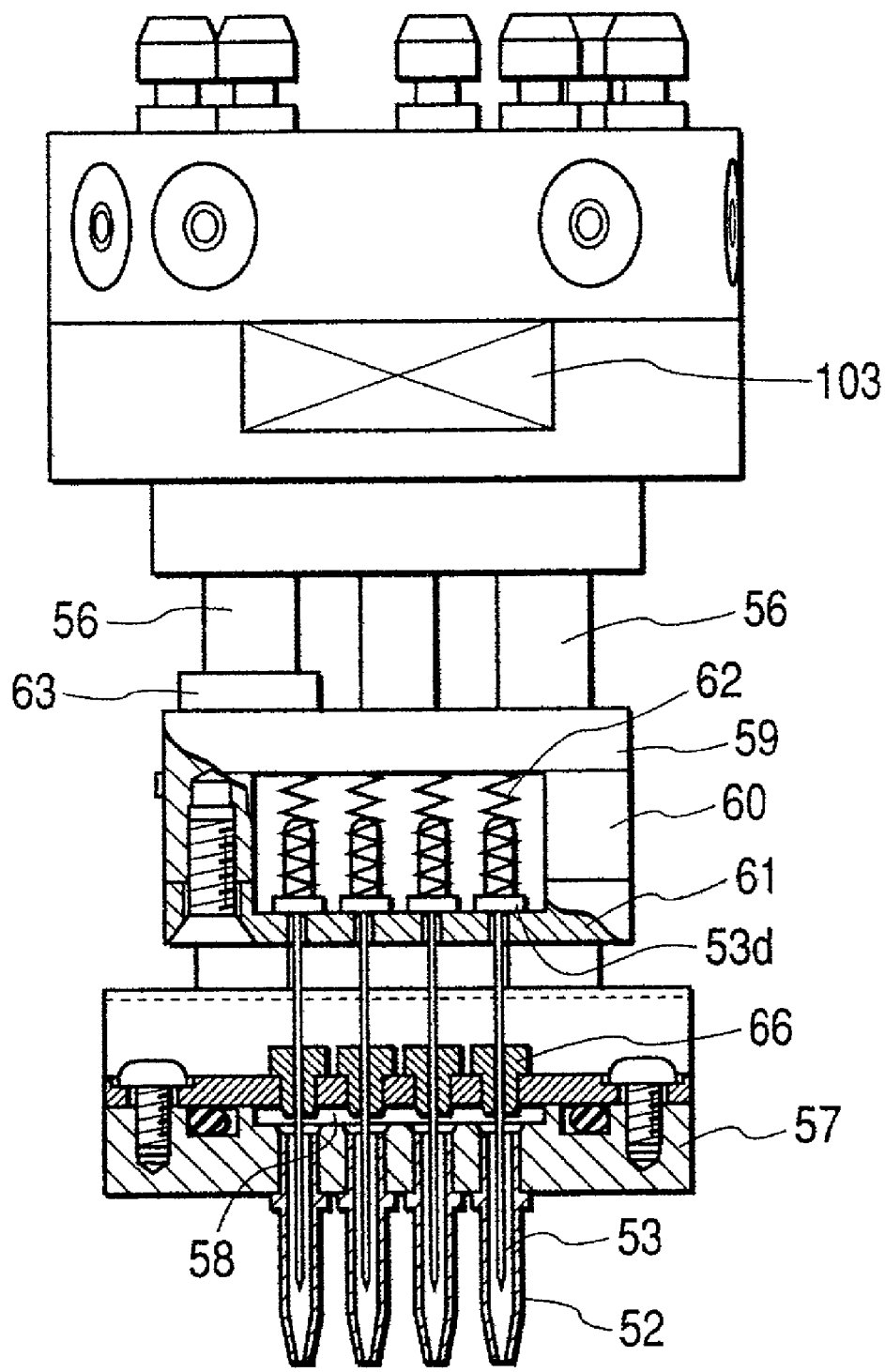
FIG. 9 is a right side view of the head, taken on line IX—IX in FIG. 8.

FIGS. 8 and 9 show the head 51 as a retaining unit. Schematically, the head 51 has a cylindrical chucked portion 54 to be attached to the chuck portion 45, a substantially rectangular upper plate 55 fixed to the lower portion of this chucked portion 54, and a substantially rectangular lower plate 57 as a base portion coupled with this upper plate 55 through a plurality of columnar supports 56 . . . .

Solution reservoir members 52 . . . as solution reservoir portions for retaining a solution to be supplied to the substrates 3 . . . are attached to the lower plate 57 lengthwise and crosswise so as to be parallel with one another. In the solution reservoir members 52 . . . , needles 53 . . . (also referred to as pins) are received as placing portions. The needles 53 are guided by a plurality of needle bushes 66 fixed to the lower plate 57 so that the needles 53 can reciprocate in the up/down direction. In this embodiment, totally 48 solution reservoir members 52 . . . and totally 48 needles 53 . . . arranged lengthwise in four lines and crosswise in 12 lines respectively are attached. Not to say, however, the number of the solution reservoir members 52 . . . and the number of the needles 53 can be set variously in accordance with the substrates 3 in which spots can be formed simultaneously.

Figure 10:
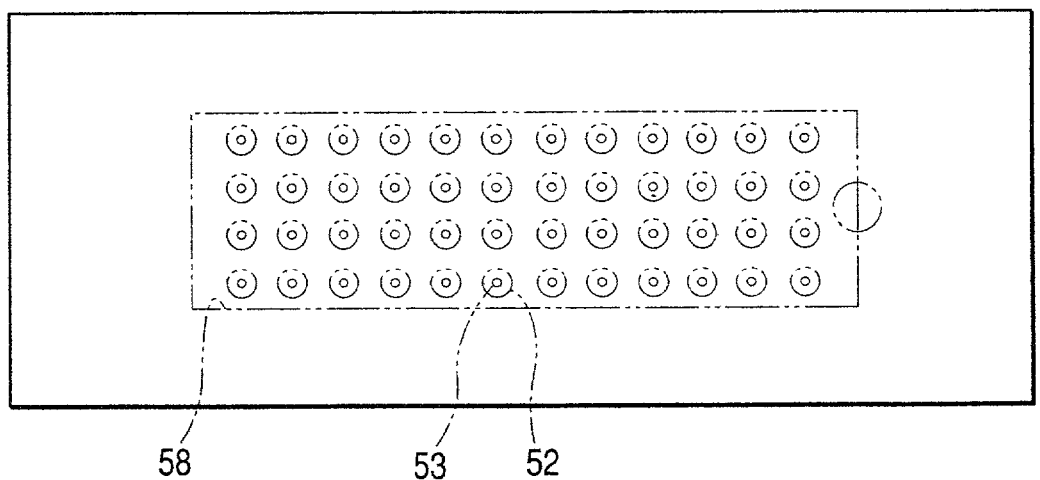
FIG. 10 is a bottom view of the head, taken on line X—X in FIG. 8.

In addition, a space 58 for supplying cleansing fluid or the like is provided in the lower plate 57 so as to extend all over the plurality of needles 53. Then, also as shown in FIG. 10, the space 58 for supplying cleansing fluid or the like communicates with all the plurality of solution reservoir members 52 . . . arranged lengthwise and crosswise.

An intermediate plate 59 is provided between the upper plate 55 and the lower plate 57 so that the intermediate plate 59 can slide relatively to the columnar supports. A needle supporting plate 61 is fixed to the lower surface of the intermediate plate 59 through a coupling portion 60. The plurality of needles 53 are supported by this needle supporting plate 61. Flanges 53d . . . to be mounted on the upper surface of the needle supporting plate 61 are formed in the upper portions of the needles 53 . . . , and coil springs 62 . . . are interposed between the flanges 53d . . . and the intermediate plate 59 respectively. The coil springs 62 . . . are compressively deformed when the needles 53 abut against the substrates 3, so that the load applied to the substrates 3 by the needles 53 is adjusted. In addition, a bush 63 for guiding the sliding motion of the intermediate plate 59 relative to the columnar supports 56 is provided in the intermediate plate 59. A coil spring 64 for lifting up the needles 53 so as to pull the needles 53 back into the solution reservoir members 52 is provided between the intermediate plate 59 and the lower plate 57.

Figure 11:
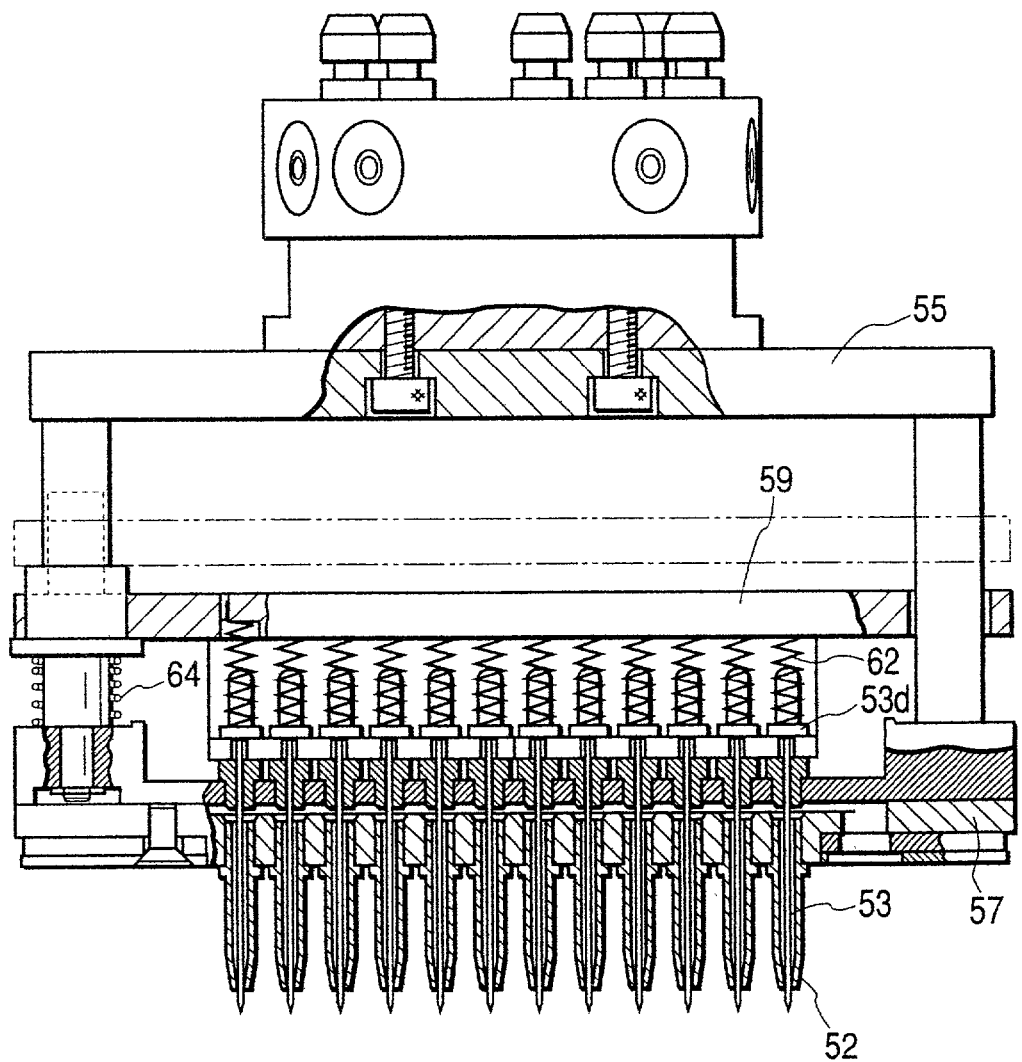
FIG. 11 is a front view of the head, showing the state where the needles protrude from solution reservoir members.

FIG. 11 shows the state where the needles 53 have moved down. When the intermediate plate 59 moves down as illustrated in FIG. 11, the needles 53 . . . also move down together with the intermediate plate 59 so that the needles 53 . . . protrude from the lower ends of the solution reservoir members 52 . . . . When the needles 53 . . . abut against the substrates 3, the coil springs 62 are compressively deformed to prevent an excessive load from being applied from the needles 53 . . . to the substrates 3 . . . .

Description will be made on the operation of the head 51 by the respective driving mechanisms. First, the head 51 is positioned in the X-direction and the Y-direction above the substrates 3 by the XY-biaxially conveying mechanism 6. Next, the head 51 as a whole is moved down by the Z1-axially driving mechanism 23Z1 so that the head 51 is positioned at a predetermined distance from the substrates in the Z-direction. Next, the L-shaped arm 42 of the Z2-axially driving mechanism 23Z2 is moved above the intermediate plate 59 in the head 51. When the L-shaped arm 42 is moved down by the Z2-axially driving mechanism 23Z2, the intermediate plate 59 is pushed down by the L-shaped arm 42 so that the needles 53 protrude from the solution reservoir members 52. On the contrary, when the L-shaped arm 42 is moved up by the Z2-axially driving mechanism 23Z2, the intermediate plate 59 is lifted up by the restoring force of the coil spring 64 so that the needles 53 are pulled back into the solution reservoir members 52.

Figure 12:
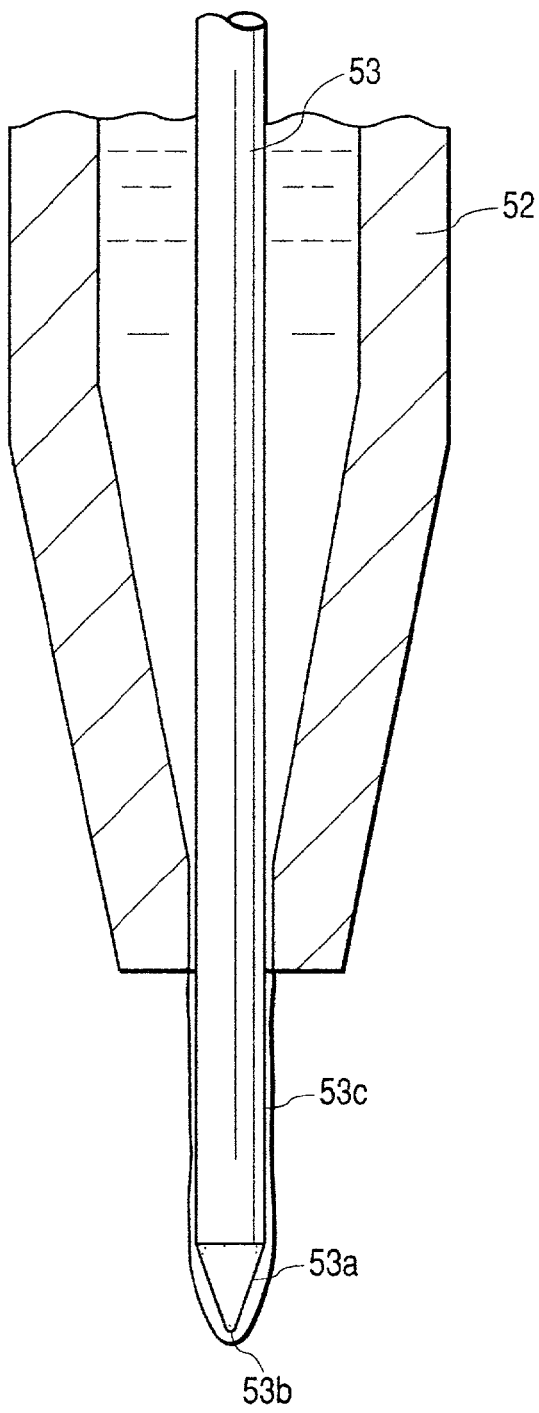
FIG. 12 is a detailed view showing a solution reservoir member and a needle.

FIG. 12 shows a solution reservoir member 52 retaining a solution, and a needle 53. The solution reservoir member 52 is formed into a tapered tubular shape so as to receive a solution and the needle 53 in its tapered internal space. The narrowest lower portion of the solution reservoir member 52 also serves to guide the up/down motion of the needle 53.

A top end portion 53a of the needle 53 is also formed into a tapered shape in its outer circumferential face. In addition, a to pend face 53b of the needle 53 to touch the substrate 3 is formed into a circular or polygonal flat face. The outer circumferential face of the top end portion 53a is made rougher in surface roughness than the outer circumferential face of a straight portion 53c and the top end face 53b of the needle 53 so that the outer circumferential face of the top end portion 53a can retain the solution. This surface roughness is set so that the solution retained on the top end face 53b is connected with the solution in the solution reservoir member 52 when the needle 53 protrudes from the solution reservoir member 52 by a predetermined amount and the top end face 53b of the needle 53 touches the substrate 3. In addition, this surface roughness is formed by grinding with a grinding stone or by electric discharge machining. For example, in the case of grinding with a grinding stone, the grinding stone is moved in the longitudinal direction of the needle 53 so as to rough the outer circumferential face of the top end portion 53a.

FIGS. 13A to 13E are process views showing a method of placing the solution retained in the solution reservoir member 52 onto the substrate 3. FIGS. 13A to 13E show the states of the solution when the needle 53 moves in the Z-axis direction (that is, up/down direction) relatively to the solution reservoir member 52.

Figure 13:
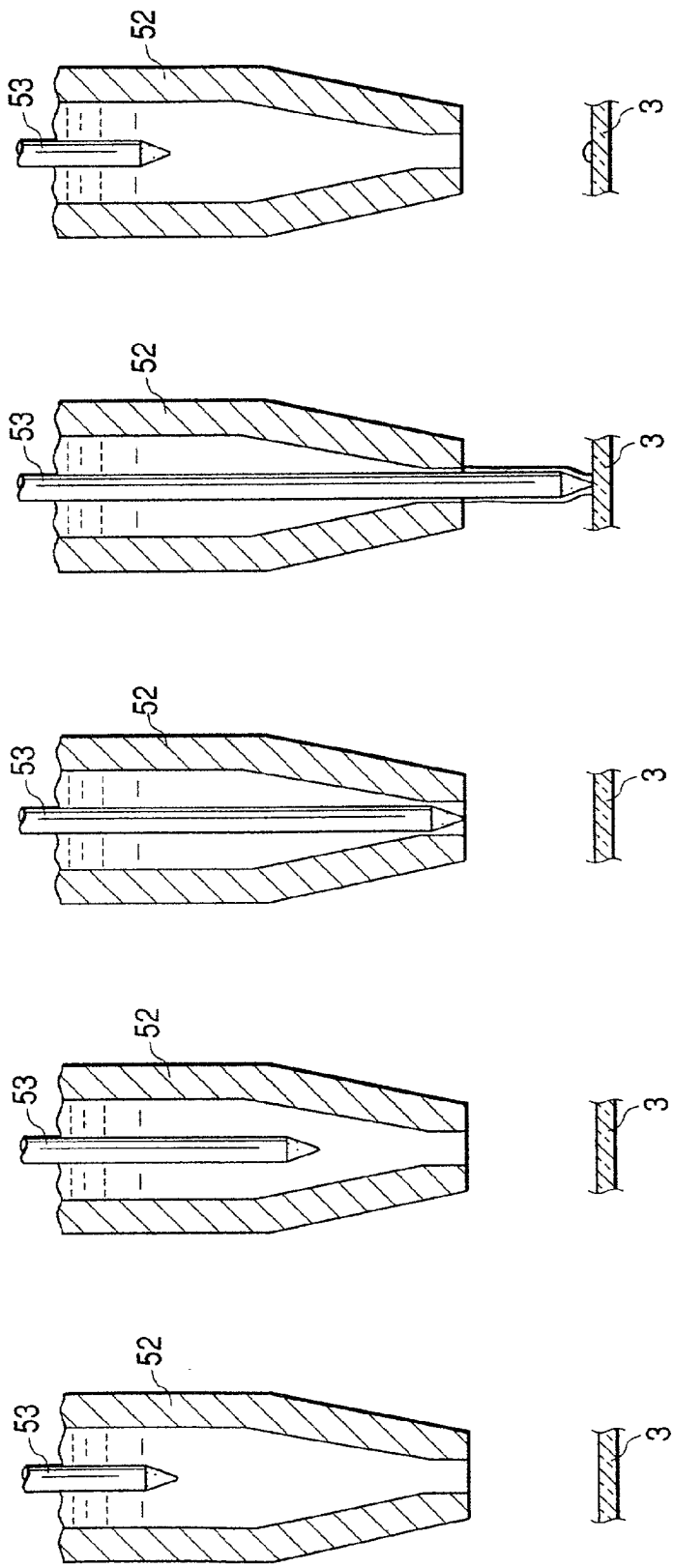
FIGS. 13A to 13E are process views showing a method in which a solution retained in a solution reservoir member is placed on a substrate.

First, as shown in FIG. 13A, the solution reservoir member 52 is positioned above the substrate 3. Next, as shown in FIGS. 13B and 13C, the needle 53 is gradually moved down relatively to the solution reservoir member 52. Next, as shown in FIG. 13D, the needle 53 is protruded from the solution reservoir member 52. At this time, the solution in the solution reservoir member 52 is drawn out by the surface tension of the solution. Then, the top end face 53b of the needle 53 is brought into contact with the substrate 3. When the top end face 53b of the needle 53 touches the substrate 3 mechanically, the solution moves from the top end face 53b of the needle 53 to the substrate 3. Thus, the solution is placed on the substrate 3. At this time, the solution retained on the top end of the needle 53 is connected with the solution in the solution reservoir member 52. As soon as the needle 53 is then pulled back from the substrate 3 as shown in FIG. 13E, a spot of the solution is formed on the substrate 3.

In such a manner, the solution retained in the solution reservoir member 52 and the solution retained on the top end of the needle 53 are integrated with each other, and the solution is drawn out of the solution reservoir member 52 and placed on the substrate 3 by use of the surface tension of the solution. Thus, the size and shape of the spot placed on the substrate 3 can be kept constant. In addition, when the outer circumferential face of the needle 53 is roughed, the amount of the solution retained on the outer circumferential face of the needle 53 is stabilized. Thus, the size and shape of the spot placed on the substrate 3 can be kept more constant.

Figure 14:
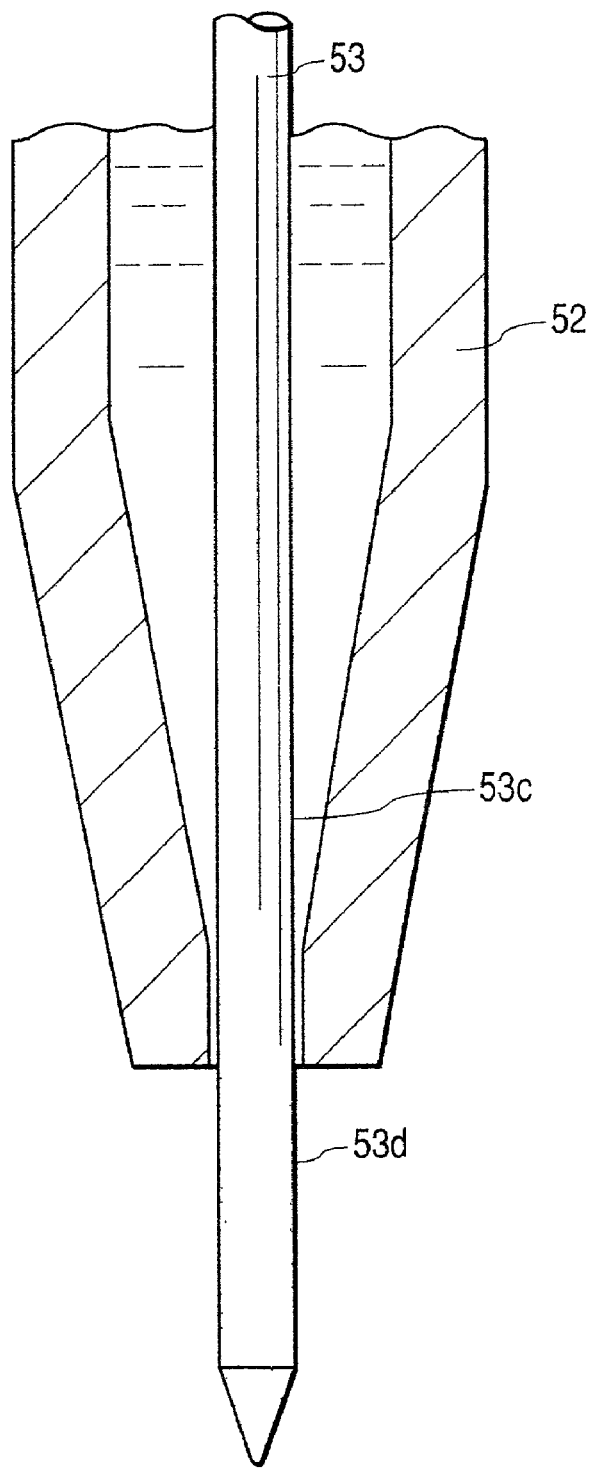
FIG. 14 is a detailed view showing another example of the solution reservoir member and the needle.

FIG. 14 shows another example of the needle 53. In this example, the surface roughness of the outer circumferential face 53d of the needle 53 protruding from the solution reservoir member 52 is made higher than the surface roughness of the outer circumferential face 53c of the needle 53 in the solution reservoir member 52. To retain a new solution different in kind from a solution which is retaining in the solution reservoir member 52, the solution having adhered to the interior of the solution reservoir member 52 and the exterior of the needle 53 has to be cleansed before the solution reservoir member 52 retains the new solution. When the portion of the needle 53 located in the solution reservoir member 52 and having no contribution to the retention of the solution is made to have its surface roughness lower than that of the protruding portion of the needle 53, it becomes easy to cleanse the exterior of the needle 53. In addition, also when the needle 53 reciprocates while sliding in the solution reservoir member 52, the needle 53 reciprocates smoothly.

Next, description will be made on the cleansing area. In this cleansing area, the head 51 which has finished forming spots is ultrasonically cleansed, then rinsed, and then dried. The cleansed head 51 retains a new or next solution of biological samples.

As shown in FIG. 1, on a cleansing table 96, there are provided an ultrasonically cleansing portion 71 as a cleansing and other treatment portion for cleansing the head 51 ultrasonically, a rinsing portion 72 as a cleansing and other treatment portion for rinsing the head 51, a drying portion 73 for drying the head 51, and a solution reservoir portion 74 for reserving a solution including biological samples. In addition, on the cleansing table 96, there is provided an XY-biaxially conveying mechanism 75 as a first conveying unit for conveying the head 51 among the ultrasonically cleansing portion 71, the rinsing portion 72, the drying portion 73 and the solution reservoir portion 74, and providing two-dimensional coordinates for the head 51.

The XY-biaxially conveying mechanism 75 is constituted by an X-axially conveying mechanism 75X and a Y-axially conveying mechanism 75Y.

As shown in FIGS. 1 and 3, the X-axially conveying mechanism 75X has a longitudinal fixed frame 81, a linear guide, a table 84 and a feeding screw 85. The fixed frame 81 is provided to extend in the X-axis direction. The linear guide is constituted by rails 82 and 82 mounted on the fixed frame 81 so as to extend in the X-axis direction, and sliders 83 and 83 set movably with respect to the rails 82 and 82. The table 84 is guided by the linear guide. The feeding screw 85 drives the table 84. The feeding screw 85 is constituted by a ball screw nut attached to the lower surface of the table 84, a screw shaft 85a screwed to the ball screw nut and extended in the X-axis direction, and an electric motor 86 for rotating this screw shaft 85a. The screw shaft 85a and the electric motor 86 are coupled with each other through a wrapping connector.

The Y-axially conveying mechanism 75Y has a longitudinal movable frame 87, a linear guide, a table 90 and a feeding screw 91. The movable frame 87 is fixed to the table 84 driven by the X-axially conveying mechanism 75X. The linear guide is constituted by a rail 88 mounted on the movable frame 87 so as to extend in the Y-axis direction, and a slider 89 incorporated movably with respect to the rail 88. The table 90 is guided by the linear guide. The feeding screw 91 drives the table 90. The feeding screw 91 is constituted by a ball screw nut attached to the lower surface of the table 90, a screw shaft 91a screwed to the ball screw nut so as to be extended in the Y-axis direction, and an electric motor 92 for rotating this screw shaft 91a. The screw shaft 91a and the electric motor 92 are coupled with each other through a wrapping connector.

As shown in FIGS. 1 and 2, a Z-axially driving mechanism 95 as a moving unit is attached to the XY-biaxially conveying mechanism 75. The Z-axially driving mechanism 95 moves the head 51 in the Z-axis direction orthogonal to the X-axis and the Y-axis, that is, in the direction orthogonal to the cleansing table 96. The Z-axially driving mechanism 95 has a Z1-axially driving mechanism 95Z1 and a Z2-axially driving mechanism 95Z2 in the same manner as the Z-axially driving mechanism 23 in the stamping area. Thus, the needles 53 can be protruded from the solution reservoir members 52 in any location among the ultrasonically cleansing portion 71, the rinsing portion 72, the drying portion 73 and the solution reservoir portion 74.

The Z1-axially driving mechanism 95Z1 is constituted by an electric actuator for moving a block by use of a feeding screw and an electric motor in the same manner as the Z1-axially driving mechanism 23Z1 in the stamping area. As shown in FIG. 6, this electric actuator has a high-rigidity outer rail 31 having a U-shape in section, and a slider 32 incorporated in the outer rail 31 so that the slider 32 can reciprocate freely. A nut is provided integrally at the center of the slider 32, and a plurality of balls 33 . . . are provided for circulating between the opposite flanks of the slider 32 and the inner flanks of the outer rail 31. Since this electric actuator has an equal rated load in any direction in which the electric actuator acts on the slider 32, the electric actuator can be used suitably as a Z-axially driving mechanism for attaching the head or the like to the slider in the state where the head or the like is overhanging.

The Z2-axially driving mechanism 95Z2 is attached to a table 97 of the Z1-axially driving mechanism 95Z1. The Z2-axially driving mechanism 95Z2 is constituted by an electric actuator in a configuration similar to that of the Z1-axially driving mechanism 95Z1, but made smaller in scale than the Z1-axially driving mechanism 95Z1. An L-shaped arm 99 for moving the needles 53 of the head 51 up/down is attached to a table 98 of the Z2-axially driving mechanism 95Z2. The L-shaped arm 99 is formed so that the L-shaped arm 99 can be plugged into the head 51 by a not-shown air cylinder. When the front end of the L-shaped arm 99 is plugged into the head and the plugged L-shaped arm 99 is moved down by the Z2-axially driving mechanism 95Z2, the needles 53 protrude from the solution reservoir members 52 of the head 51.

In addition, a slewing motor 100 as a slewing portion is attached to the table 97 of the Z1-axially driving mechanism 95Z1. A disc 101 slewing in a horizontal plane is attached to the output shaft of the slewing motor 100. A pair of clamps 102 and 102 as grasping portions which can grasp the head 51 are attached to the lower surface of the disc 101 at a distance of 180 degrees with each other. The clamps 102 and 102 are opened/closed by a not-shown air cylinder or the like so as to clamp a flat portion 103 (see FIGS. 8 and 9) formed in the outer circumference of the head 51.

The head 51 conveyed by the XY-biaxially conveying mechanism 75 in the cleansing area has the same configuration as that of the head 51 conveyed by the XY-biaxially conveying mechanism 6 in the stamping area. Thus, same parts are referenced correspondingly, and their description will be therefore omitted.

The slewing motor 100 slews 180 degrees every time so that a head 51 is delivered from the XY-biaxially conveying mechanism 6 in the stamping area to the XY-biaxially conveying mechanism 75 in the cleansing area, and another head 51 is delivered from the XY-biaxially conveying mechanism 75 in the cleansing area to the XY-biaxially conveying mechanism 6 in the stamping area.

Specifically, as shown in FIGS. 1 and 2, a head 51 which has finished forming spots is first conveyed to the delivery position 104 by the XY-biaxially conveying mechanism 6 in the stamping area. On the other hand, a head 51 retaining a new solution is conveyed to a waiting position 105 by the XY-biaxially conveying mechanism 75 in the cleaning area. The waiting position 105 is shifted by 180 degrees from the delivery position 104. At this time, an empty clamp which does not grasp any head is located in the delivery position 104. Next, the clamp 102 of the XY-biaxially conveying mechanism 75 in the cleansing area grasps the head 51 which has finished forming spots and been conveyed to the delivery position 104. Thus, the head is delivered from the XY-biaxially conveying mechanism 6 in the stamping area to the XY-biaxially conveying mechanism 75 in the cleansing area. Next, the slewing motor 100 slews the disc 101 by 180 degrees so that the head 51 which has finished forming spots is placed in the waiting position 105 while the head 51 retaining the new solution is placed in the delivery position 104. Next, the chuck portion 45 of the XY-biaxially conveying mechanism 6 in the stamping area grasps the head 51 retaining the new solution. Thus, the head is delivered from the XY-biaxially conveying mechanism 75 in the cleansing area to the XY-biaxially conveying mechanism 6 in the stamping area.

Since the heads 51 can be delivered between the XY-biaxially conveying mechanism 6 in the stamping area and the XY-biaxially conveying mechanism 75 in the cleansing area in such a manner, cleansing and other treatment can be carried out on one head 51 while spots are formed on the substrates 3 by the other head 51. The work of forming spots on substrates can be kept in succession except the moment when heads 51 and 51 are delivered between the XY-biaxially conveying mechanism 6 in the stamping area and the XY-biaxially conveying mechanism 75 in the cleansing area. Thus, microarrays can be produced extremely efficiently. In addition, heads 51 and 51 are delivered between the XY-biaxially conveying mechanism 6 in the stamping area and the XY-biaxially conveying mechanism 75 in the cleansing area directly without being once left on the apparatus. Thus, the work of delivery can be performed more efficiently without producing a useless waiting time.

Incidentally, although the pair of clamps 102 and 102 and the slewing motor 100 are provided on the side of the XY-biaxially conveying mechanism 75 in the cleansing area in the above embodiment, they may be provided on the side of the XY-biaxially conveying mechanism 6 in the stamping area. Further, if a slight waiting time is allowed, a turn table may be provided on the apparatus so that heads 51 are delivered through this turn table.

The head which has finished forming spots is conveyed to the ultrasonically cleansing portion 71 by the XY-biaxially conveying mechanism 75 in the cleansing area. In the ultrasonically cleansing portion 71, the solution reservoir members 52 are immersed in pure water applied with ultrasonic vibration so that the exteriors of the solution reservoir members 52 are cleansed. Incidentally, in the ultrasonically cleansing portion 71, it is desired that the exteriors of the needles 53 are also cleansed in the state that the needles 53 are protruded from the solution reservoir members 52.

The head 51 ultrasonically cleansed is conveyed to the rinsing portion 72 by the XY-biaxially conveying mechanism 75. The rinsing portion 72 rinses the interiors and exteriors of the solution reservoir members 52 and the exteriors of the needles 53.

The head 51 is set in a pure water tank in which ultrapure water is stored as cleansing fluid, so that the solution reservoir members 52 are immersed in the ultrapure water. Thus, the exteriors of the solution reservoir members 52 are cleansed. In addition, when the head 51 is set in the pure water tank, a pure water supply pipe 108 (see FIG. 8) provided in the pure water tank is connected to the head 51 so that the pure water supply pipe 108 communicates with the space 58 for supplying cleansing fluid or the like. As shown in FIG. 8, the space 58 for supplying cleansing fluid or the like is provided in the lower plate 57 of the head 51 correspondingly to the rear ends of the solution reservoir members 52. The space 58 for supplying cleansing fluid or the like is formed as a single broad space extending over the respective solution reservoir members 52. When the pure water with pressure is supplied from the pure water supply pipe 108, the pure water spreads in this single space. The pure water charged into the single space is supplied to the respective solution reservoir members 52.

By cleansing the solution reservoir members 52 . . . while applying pressure to the interiors of the solution reservoir members 52 . . . , the cleansing time can be shortened, for example, in comparison with the case where the solution is softened in water and removed without pressure applied thereto. In addition, since the single space is formed over the plurality of the solution reservoir members 52, the loss in pressure of the pure water supplied into the plurality of the solution reservoir members 52 . . . is reduced, and the loss in pressure becomes substantially homogeneous among the respective solution reservoir members 52 . . . . Accordingly, the interiors of the plurality of the solution reservoir members 52 . . . and the exteriors of the plurality of the needles 53 . . . can be cleansed with substantially homogeneous pressure applied thereto.

As shown in FIG. 1, the head 51 rinsed is conveyed to the drying portion 73 by the XY-biaxially conveying mechanism 75. In this drying portion 73, the interiors and exteriors of the solution reservoir members 52 and the exteriors of the needles 53 are dried.

Figure 15:
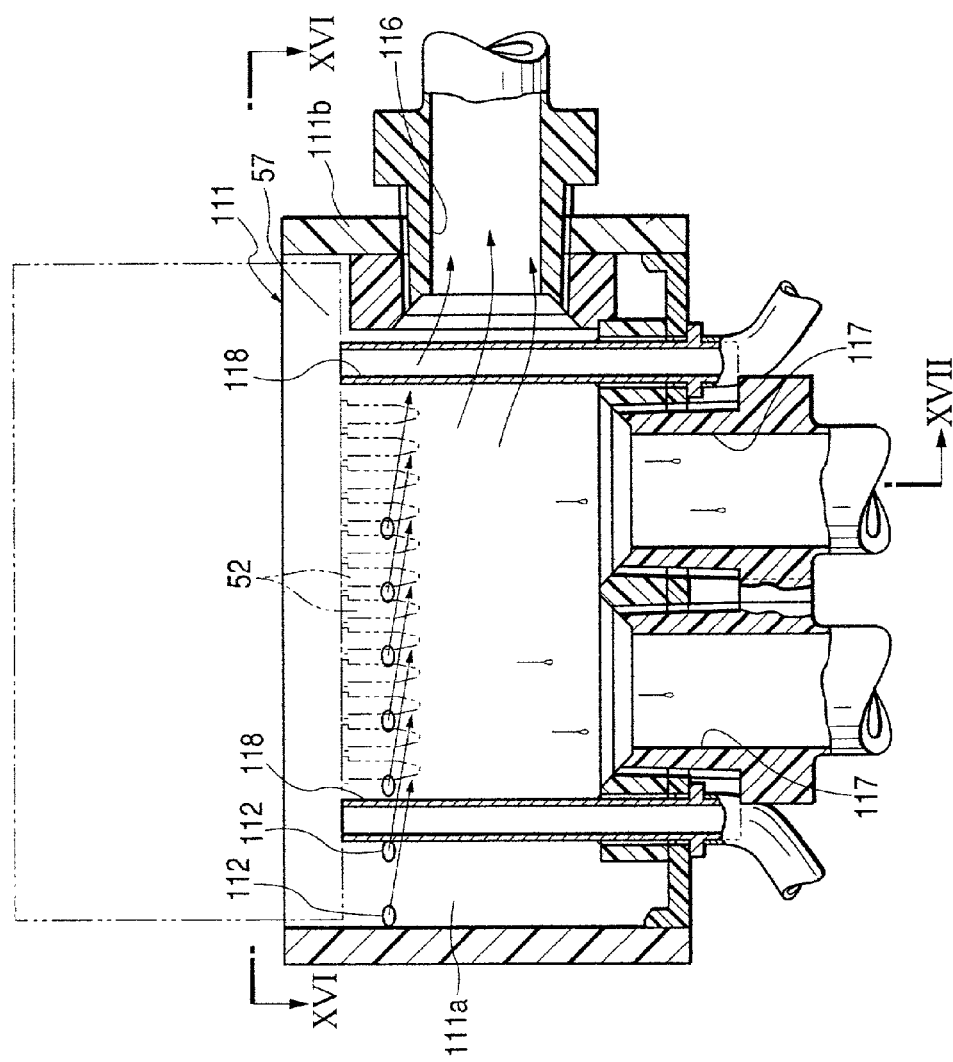
FIG. 15 is a sectional view showing a drying portion.
Figure 16:
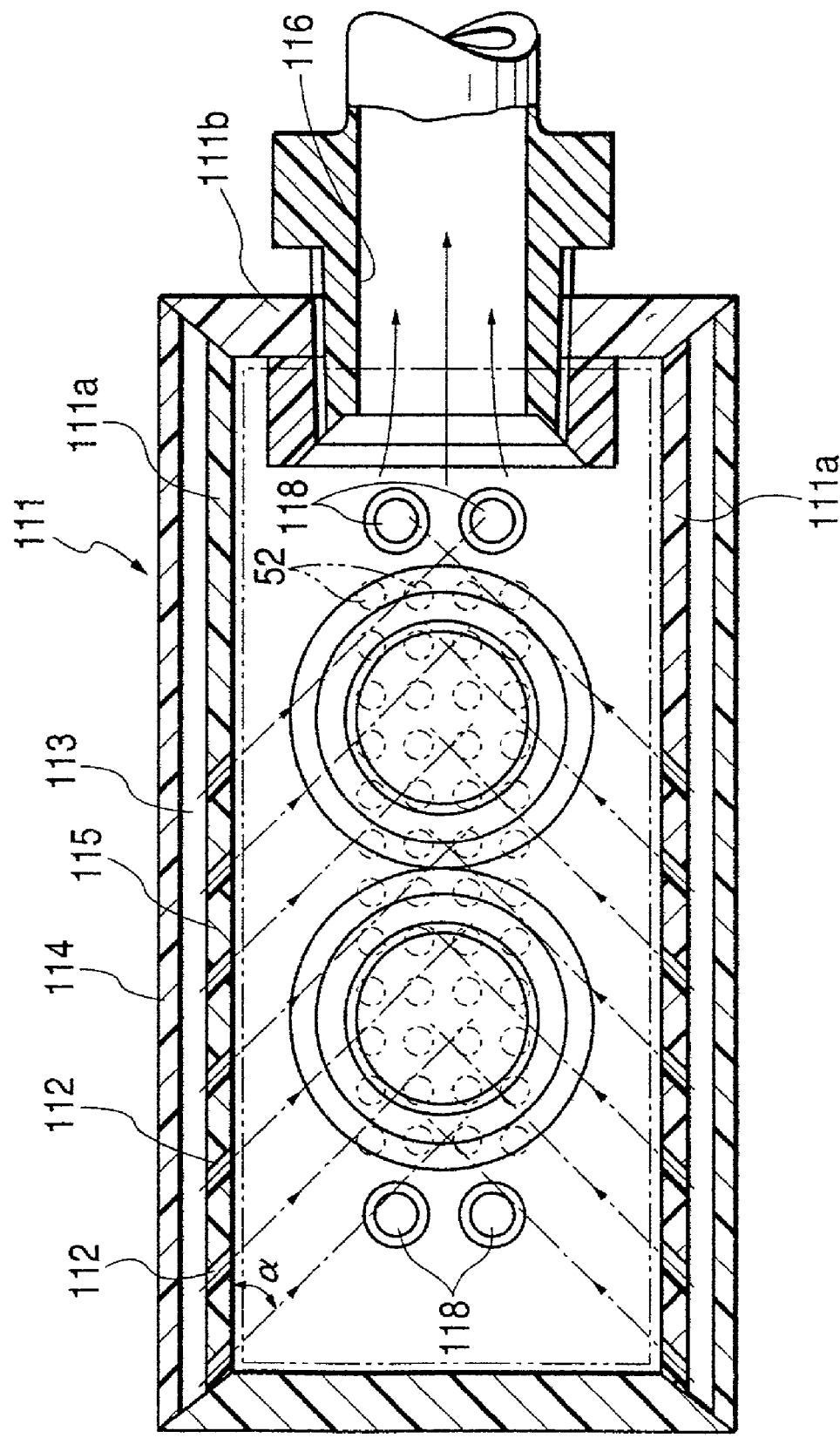
FIG. 16 is a plan view of the drying portion, taken on line XVI—XVI in FIG. 15.
Figure 17:
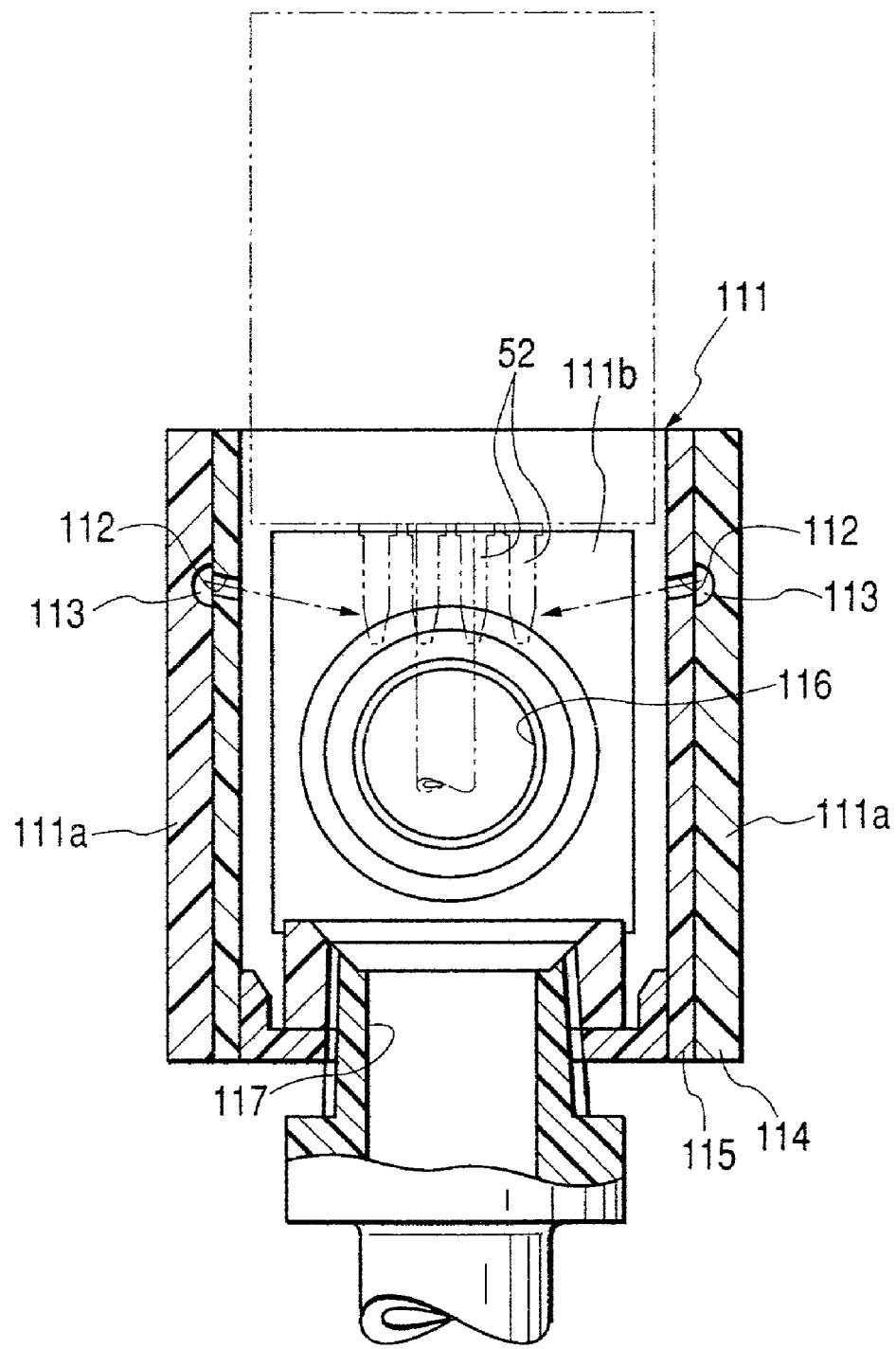
FIG. 17 is a sectional view of the drying portion, taken on line XVII—XVII in FIG. 15.

FIGS. 15 to 17 show the drying portion 73. The drying portion 73 has a substantially rectangular parallelepiped drying tank 111 whose upper portion is opened. The head 51 is set in the upper space of the drying tank 111 so that the upper portion of the drying tank 111 is closed by the lower plate 57 of the head 51. On two opposed walls 111a and 111a of the drying tank 111, a plurality of nozzles 112 and 112 for spouting compressed air obliquely with respect to the wall surfaces are provided. Each nozzle 112 spouts the air slightly downward with respect to the horizontal direction. On a plane, the angle α with which the wall surfaces of the opposed walls 111a and 111a intersect the directions of the air spouted from the respective nozzles 112 is about 45 degrees. In addition, the nozzles 112 are disposed symmetrically with respect to the solution reservoir members.

An air supply channel 113 is connected to the nozzles 112 . . . . The nozzles 112 . . . and the air supply channel 113 are formed by putting two plastic boards 114 and 115 together. The air supply channel 113 is formed in the outside board 114 so as to have a substantially semicircular shape in section and extend along the outside board 114. In the inside board 115, holes are formed obliquely to the board 115 so as to form the nozzles 112 . . . . When the outside board 114 and the inside board 115 are put together, the nozzles 112 and the air supply channel 113 are formed.

In addition, an air outlet 116 is provided in a wall 111b intersecting the opposite walls 111a and 111a on the downstream side of the air flow. In the bottom portion of the drying tank 111, drain ports 117 and 117 are provided for draining misty cleansing water removed from the solution reservoir members 52 and the needles 53. In the drying tank 111, air pipe arrangement 118 is provided for drying the interiors of the solution reservoir members 52. When the head 51 is set in the drying tank 111, the air pipe arrangement 118 communicates with the space 58 for supplying cleansing fluid or the like (see FIG. 8). Since the space 58 for supplying cleansing fluid or the like is formed as a single broad space extending over the plurality of the solution reservoir members 52, the drying air is supplied to the interiors of the respective solution reservoir members 52 through the space 58 for supplying cleansing fluid when the compressed air is supplied from the air pipe arrangement 118.

Since the flow of the spouted air is made oblique to the wall surfaces of the opposite walls 111a and 111a and the air outlet 116 is provided on the downstream side of the flow, a flow of the air having directionality into the drying tank 111 is generated. As a result, all the cleansing fluid mixed with the solution blown out of the surfaces of the solution reservoir members 52 and the needles 53 by the air goes on the flow so as to be drained to the outside of the drying tank 111. Thus, the cleansing fluid is prevented from reattachment.

On the contrary, if the air were blown against the solution reservoir members 52 and the needles 53 simply without providing the air outlet 116, residual cleansing fluid flying about together with the air would bounce from the wall surface of the drying tank 111 or the like so that the residual cleansing fluid might re-adhere to the solution reservoir members 52 or the needles 53. The re-adherence generated would lead not only to an obstacle to efficient drying but also to a fear that a new solution might be mixed with the reattached cleansing fluid.

In addition, in the head 51, the solution reservoir members 52 and the needles 53 are arranged lengthwise and crosswise in parallel with one another. When the flow of the spouted air is made oblique to the wall surfaces of the opposite walls 111a and 111a, the air becomes easy to reach the portion which is in the shadow viewed from the wall surfaces, in comparison with the case where the flow is set at right angles with the wall surfaces. Accordingly, the plurality of the solution reservoir members 52 and the plurality of the needles 53 can be dried uniformly.

As shown in FIGS. 1 and 2, the head 51 dried is conveyed to the solution reservoir portion 74 by the XY-biaxially conveying mechanism 75. The solution reservoir portion 74 has a cassette 122 receiving a plurality of titer plates 121 . . . as solution retaining plates for retaining solutions, and a plate conveying mechanism 123 for extracting a titer plate 121 from the cassette 122 and conveying the extracted titer plate 121 to a load position 132. In this solution reservoir portion 74, a new solution of biological samples is charged into the head 51 which has been cleansed. The operation in which the head 51 is immersed in a solution so as to suck the solution is referred to as "load".

A plurality (for example, 384) of recess portions are arranged in each titer plate 121, and the solution of biological samples is retained in these recess portions. For example, when the head has 48 solution retaining members, 8 loads can be carried out in one titer plate. The same kind of solution may be charged into the plurality of recess portions, or different kinds of solutions may be charged therein.

A plurality (for example, 10) of titer plates 121 . . . are received in the cassette 122 at an equal interval in the Z-axis direction (that is, up/down direction). Two cassettes 122 are provided in the upper and lower of the cleansing table 96. Thus, 20 titer plates 121 in total are received in this apparatus. In each of the cassettes 122, an opening for taking the titer plates 121 in and out is formed on the conveying mechanism 123 side. In addition, a grip 125 to be gripped by human hand is provided on the top of each of the cassettes 122.

Each of the cassettes 122 is mounted on a cassette support table 124 slidably attached to the apparatus. The cassette 122 is incorporated in the apparatus by pulling out the cassette support table 124 manually, mounting the cassette 122 on the cassette support table 124, and bringing the cassette support table 124 back to its original position manually.

The plate conveying mechanism 123 is constituted by a Z-axially driving mechanism 123Z, a Y-axially driving mechanism 123Y and an X-axially driving mechanism 123X. The Z-axially driving mechanism 123Z has the same configuration as the electric actuator for moving a slider by use of a feeding screw and an electric motor. The Z-axially driving mechanism 123Z moves a support plate 126 supporting a titer plate 121 vertically between the highest titer plate 121 and the lowest titer plate 121.

The X-axially driving mechanism 123X is attached to a table 127 of the Z-axially driving mechanism 123Z. This X-axially driving mechanism 123X is constituted by a so-called rodless cylinder. The rodless cylinder has a track rail 128 extending in the X-axis direction, and a table 129 which can slide on the track rail 128. The rodless cylinder uses the air as a driving source to move the table 129 in the X-axis direction. Stoppers for positioning the table 129 are provided at the both ends of the track rail 128.

The Y-axially driving mechanism 123Y is attached to the table 129 of the X-axially driving mechanism 123X. This Y-axially driving mechanism 123Y is also constituted by a so-called rodless cylinder, which moves a table 130 in the Y-axis direction while positioning the table 130 in two positions in the Y-axis direction. The support plate 126 for supporting the titer plate 121 is attached to the table 130 of the Y-axially driving mechanism 123Y.

In addition, a sucker 131 for removing a cover put on the titer plate 121 is attached to the table 130. Each titer plate 121 is covered with a cover for preventing the moisture of the solution from evaporating. Since this cover becomes an obstacle during a load, the cover is sucked on the sucker 131 and shunted upward by a not-shown moving mechanism such as an electric actuator.

Description will be made on the operation of the plate conveying mechanism 123 for extracting an aimed titer plate 121 from the plurality of titer plates 121 . . . .

First, the plate conveying mechanism 123 uses the Z-axially driving mechanism 123Z to move the support plate 126 in the Z-axis direction so that the support plate 126 is located slightly under the aimed titer plate 121. Next, the X-axially driving mechanism 123X is driven to insert the support plate 126 into the cassette 122. Next, the Z-axially driving mechanism 123Z is driven again to move the support plate 126 upward slightly so as to lift up the titer plate 121. Then, the X-axially driving mechanism 123X is driven again to extract the titer plate 121 from the cassette 122. Then, the titer plate 121 is conveyed to the load position 132. Incidentally, such an operation of the conveying mechanism is executed by a not-shown controller.

After the titer plate 121 is conveyed to the load position 132, the head 51 cleansed and dried is also conveyed to the load position by the two-dimensionally conveying mechanism 75. In this load position 132, the solution reservoir members 52 are immersed in the solution of biological samples so as to suck the solution.

Description will be made on the method for sucking the solution. First, the solution reservoir members 52 are plugged into the recess portions in the titer plate 121 so that the top ends of the solution reservoir members 52 are immersed in the solution. Next, when the needles 53 are moved up while the positions of the solution reservoir members 52 are fixed, the solution is drawn up with the elevation of the needles 53 so that the solution reservoir members 52 are filled with the solution. When the solution reservoir members 52 and the needles 53 are lifted up in this state, the solution charged into the solution reservoir members is retained as it is.

A head place 135 is provided on the cleansing table 96. The head 51 is first placed on this head place 135. The operation of the apparatus begins with the XY-biaxially conveying mechanism 75 in the cleansing area so that XY-biaxially conveying mechanism 75 goes for the head 51 placed on the head place 135.

Next, the whole operation of the microarrayer according to this embodiment will be described along the procedure for producing microarrays. Incidentally, in the following steps, the XY-biaxially conveying mechanism 6 and the Z-axially driving mechanism 23 in the stamping area, and the XY-biaxially conveying mechanism 75 and the Z-axially driving mechanism 95 in the cleansing area are operated appropriately so that the heads 51 are positioned sequentially in given positions. Such control is executed by a not-shown controller.

First, as a preliminary stage, a plurality of substrates 3 . . . are arranged in the stamping area, and a vacuum system is actuated to suck and fix the substrates 3 . . . . A substrate for forming a microarray on trial or a dummy substrate is fixed onto the test table 5. On the other hand, a plurality of titer plates 121 . . . are received in the cassettes 122 of the solution reservoir portion 74 in the cleansing area. For example, a plurality of kinds of solutions of DNA fragments are put into the respective recess portions of the titer plates 121 . . . .

Next, the XY-biaxially conveying mechanism 75 in the cleansing area goes for the head 51 placed on the head place 135. Here, of the pair of clamps 102 and 102, only one clamp 102 grasps the head 51.

Next, the XY-biaxially conveying mechanism 75 conveys the grasped head 51 to the load position 132. Here, a load step for sucking a solution into the solution reservoir members 52 is carried out. The plate conveying mechanism 123 conveys a titer plate 121 having a required solution to the load position 132 before the head 51 is conveyed to the load position 132. After the XY-biaxially conveying mechanism 75 conveys the grasped head 51 to the load position 132, the Z-axially driving mechanism 123Z in the cleansing area lifts the solution reservoir members 52 and the needles 53 up and down so as to allow the solution reservoir members 52 to suck the solution.

Next, the XY-biaxially conveying mechanism 75 in the cleansing area conveys the head 51 retaining the solution to the delivery position 104.

Next, the XY-biaxially conveying mechanism 6 in the stamping area conveys the empty chuck portion 45 to the delivery position 104. Then, the Z1-axially driving mechanism in the stamping area moves down the chuck portion 45 so that the head retaining the solution is grasped by the chuck portion 45. Thus, the head is delivered from the XY-biaxially conveying mechanism 75 in the cleansing area to the XY-biaxially conveying mechanism 6 in the stamping area.

Next, the XY-biaxially conveying mechanism 6 in the stamping area conveys the head 51 onto the test table 5. A test step for adjusting the amount of the solution adhering to the needles 53 is carried out in this test table 5. In the test step, the Z-axially driving mechanism in the stamping area stamps the needles 53 onto a substrate 3 so that the solution adhering to the needles 53 excessively is flicked off the needles 53.

After the completion of the test step, a stamping step for forming spots on substrates 3 is carried out. In this stamping step, first, the XY-biaxially conveying mechanism 6 in the stamping area moves the head 51 to a spot formation position on a substrate 3. Then, the Z1-axially driving mechanism 23Z1 in the stamping area moves down the head 51 so as to position the head 51 slightly above the substrate 3. Next, the Z2-axially driving mechanism 23Z2 in the stamping area protrudes the needles 53 from the solution reservoir member 3 and stamps the needles 53 onto the substrate 3.

After spots are formed on the given substrate, the XY-biaxially driving mechanism in the stamping area moves the head to the next substrate. Then, the stamping step is repeated again.

While the XY-biaxially driving mechanism 6 in the stamping area is repeating the stamping step, the XY-biaxially driving mechanism 75 in the cleansing area grasps the rest head 51 placed on the head place 135 and conveys the head 51 to the load position 132. In this load position 132, a load step for sucking a solution into the solution reservoir members 52 is carried out. Then, the XY-biaxially driving mechanism 75 in the cleansing area conveys the head 51 retaining the solution to the waiting position 105. At this time, the empty clamp 102 grasping no head is located in the delivery position 104.

After spots have been formed on all the substrates 3 . . . on the working table 4, the XY-biaxially driving mechanism 6 in the stamping area conveys the head 51, which has finished forming spots, to the delivery position 104. Then, the heads 51 and 51 grasped by the XY-biaxially driving mechanism 6 in the stamping area and the XY-biaxially driving mechanism 75 in the cleansing area are delivered to each other.

Description will be made on this delivery step. First, the empty clamp 102 provided in the XY-biaxially driving mechanism 75 in the cleansing area grasps the head 51 which has finished forming spots and which has been conveyed to the delivery position 104. Thus, the head 51 which has finished forming spots is delivered from the XY-biaxially driving mechanism 6 in the stamping area to the XY-biaxially driving mechanism 75 in the cleansing area. Next, the slewing motor 100 positions the head 51 which has finished forming spots to the waiting position 105 while positioning the head 51 retaining a new solution to the delivery position 104. Next, the chuck portion 45 provided in the XY-biaxially driving mechanism 6 in the stamping area grasps the head 51 retaining the new solution. Thus, the head 51 is delivered from the XY-biaxially driving mechanism 75 in the cleansing area to the XY-biaxially driving mechanism 6 in the stamping area.

The XY-biaxially driving mechanism 6 in the stamping area after the XY-biaxially driving mechanism 6 has terminated the delivery step conveys the head 51 onto substrates again. Then, the test step and the stamping step are carried out.

The XY-biaxially driving mechanism 75 in the cleansing area after the XY-biaxially driving mechanism 75 has terminated the delivery step carries out a cleansing step at the same time that the XY-biaxially driving mechanism 6 in the stamping area carries out the test step and the stamping step. In this cleansing step, first, the head 51 which has finished forming spots is conveyed to the ultrasonically cleansing portion 71 so that the exteriors of the solution reservoir members 52 are cleansed ultrasonically. Then, the head 51 is conveyed to the rinsing portion 72 so that the interiors and exteriors of the solution reservoir members 52 and the needles 53 are rinsed. After that, the head 51 is conveyed to the drying portion 73 so that the solution reservoir members 52 and the needles 53 are dried.

The XY-biaxially driving mechanism 75 in the cleansing area conveys the cleansed head 51 to the load position 132 again. In this load position, the load step for sucking a new solution into the cleansed head 51 is carried out again.

Subsequently, the XY-biaxially driving mechanism 6 in the stamping area executes the head delivery step, the test step and the stamping step sequentially. On the other hand, the XY-biaxially driving mechanism 75 in the cleansing area executes the head delivery step, the cleansing step and the load step sequentially.

In such a manner, when one head 51 conveyed by the XY-biaxially driving mechanism 6 in the stamping area is forming spots on substrates 3 . . . , the other head 51 conveyed by the XY-biaxially driving mechanism 75 in the cleansing area is cleansed and dried. Thus, it is possible to keep the stamping step for forming spots on substrates 3 . . . in succession, so that it is possible to produce microarrays extremely efficiently.

Incidentally, the embodiment has shown the case where a retaining unit (head) is provided with needles and solution reservoir members. However, a retaining unit having only needles may be adopted.

As described above, according to the invention, a microarraying head is constituted by a base portion and a plurality of placing portions arranged in parallel with one another on the base portion, and a broad space for supplying cleansing fluid or the like is provided to extend all over the plurality of placing portions. Accordingly, all the plurality of placing portions can be cleansed with substantially uniform pressure applied thereto. It is therefore possible to cleanse all the plurality of placing portions surely in a short time.

Also, according to the invention, a microarraying head is prepared for each of an area for forming spots and an area for cleansing and drying, so that the microarraying heads can be delivered between the area for forming spots and the area for cleansing and drying. Thus, cleansing and other treatment can be carried out on one microarraying head conveyed by a first conveying unit while spots are formed on substrates by the other microarraying head conveyed by a second conveying unit. Since the work of forming spots on substrates can be kept in succession except the moment when the retaining units are delivered between the first conveying unit and the second conveying unit, microarrays can be produced extremely efficiently.

What is claimed is:
1. A microarraying head for retaining a solution including biological samples, and forming spots of said solution on substrates, said microarraying head comprising:
 a base portion;
 a plurality of placing portions arranged in parallel with one another on said base portion and for placing said solution on said substrates with top ends of said placing portions touching said substrates;
 a plurality of solution reservoir portions for retaining said solution including said biological samples;

wherein said placing portions project from and retreat to said solution reservoir portions so as to place said solution retained in said solution reservoir portions onto said substrates;

wherein said solution reservoir portions are attached to said base portion; and wherein a space for supplying cleansing fluid is provided in said base portion; said space communicates with said solution reservoir portions so as to allow said cleansing fluid to flow over all of said plurality of placing portions.

2. The microarraying head according to claim 1, wherein said placing portions are arranged lengthwise and crosswise on said base portion.

3. A microarrayer comprising:

a solution reservoir portion for retaining a solution including biological samples;

a working table on which a plurality of substrates can be arrayed;

a solution retaining unit for retaining said solution taken in from said solution reservoir portion, and forming spots of said solution on said substrates;

a cleansing and other treatment portion for carrying out cleansing and other treatment on said retaining unit;

a moving unit for moving said retaining unit close to/far from said substrates and making said retaining unit form spots on said substrates; and a conveying unit for conveying said retaining unit in an area including said solution reservoir portion, said working table and said cleansing and other treatment portion, and providing two-dimensional coordinates for said retaining unit;

wherein said retaining unit has a base portion, and a plurality of placing portions arranged in parallel with one another on said base portion and for placing said solution on said substrates with top ends of said placing portions touching said substrates; and wherein a space for supplying cleansing fluid is provided in said base portion so as to allow said cleansing fluid to flow over all of said plurality of placing portions.

4. A microarrayer comprising:

a solution reservoir portion for retaining a solution including biological samples;

a working table on which a plurality of substrates can be arrayed;

a plurality of retaining units for retaining said solution taken in from said solution reservoir portion, and forming spots of said solution on said substrates;

a cleansing and other treatment portion for carrying out cleansing and other treatment on one of said retaining units;

a conveying unit for conveying one of said retaining units in an area including said solution reservoir portion, said working table and said cleansing and other treatment portion, and providing two-dimensional coordinates for said retaining unit;

wherein said conveying unit has a first conveying unit for conveying one of said retaining units onto said cleansing and other treatment portion, and a second conveying unit for conveying one of said retaining units onto said working table;

wherein each retaining unit has a base portion, and a plurality of placing portions arranged in parallel with one another on said base portion;

wherein a space for supplying cleansing fluid is provided in said base portion so as to allow said cleansing fluid to flow over all of said plurality of placing portions; and wherein said retaining units can be delivered between said first conveying unit and said second conveying unit by a delivery unit.

5. The microarrayer according to claim 4, further comprising:

a moving unit for moving one of said retaining units close to/far from said substrates and making said retaining unit form spots on said substrates;

wherein each of said retaining units can be attached to said moving unit removably.

6. A microarrayer according to claim 4, wherein one of said first conveying unit and said second conveying unit has a plurality of grasping portions for grasping said retaining units, and a slewing portion for slewing said plurality of grasping portions; and said slewing portion slews so that delivery of said retaining unit from said first conveying unit to said second conveying unit and delivery of said retaining unit from said second conveying unit to said first conveying unit are carried out in predetermined positions respectively.

7. The microarrayer according to claim 4, further comprising:

a detection unit for detecting at least one of a posture and a position of said retaining unit supported by said second conveying unit;

a posture changing unit for changing said at least one of said posture and said position of said retaining unit with respect to said second conveying unit; and a control unit for operating said posture changing unit based on said posture of said retaining unit detected by said detection unit.

8. The microarrayer according to claim 4, wherein said solution reservoir portion has a plurality of solution retaining plates for retaining said solution, a cassette for receiving said solution retaining plates, and a plate conveying mechanism for extracting one of said solution retaining plates from said cassette and conveying said extracted solution retaining plate to a predetermined position.

9. A microarraying process for sequencing spots of a solution of biological samples on substrates, comprising:

a cleansing step of using a first conveying unit to convey a first microarraying head, and carrying out cleansing and other treatment on said first microarraying head;

a stamping step of taking in and retaining a solution, using a second conveying unit to convey a second microarraying head for forming spots of said solution on said substrates, and forming spots of said solution of biological samples on said substrates; and a delivering step for delivering microarraying heads between said first conveying unit and said second conveying unit, wherein said first microarraying head being supported by said first conveying unit is delivered to said second conveying unit, and said second microarraying head being supported by said second conveying unit is delivered to said first conveying unit;

wherein said stamping step and said cleansing step are carried out simultaneously and before or after said delivering step.

* * * * *